(12) United States Patent
Nevola et al.

(10) Patent No.: US 11,352,395 B2
(45) Date of Patent: Jun. 7, 2022

(54) ANTICANCER PEPTIDES

(71) Applicant: IDP DISCOVERY PHARMA, S.L., Barcelona (ES)

(72) Inventors: Laura Nevola, Barcelona (ES); Santiago Esteban Martín, Barcelona (ES)

(73) Assignee: IDP DISCOVERY PHARMA, S.L., Barcelona (ES)

( * ) Notice: Subject to any disclaimer, the term of this patent is extended or adjusted under 35 U.S.C. 154(b) by 0 days.

(21) Appl. No.: 16/635,902

(22) PCT Filed: Jul. 31, 2018

(86) PCT No.: PCT/EP2018/070714
§ 371 (c)(1),
(2) Date: Jan. 31, 2020

(87) PCT Pub. No.: WO2019/025432
PCT Pub. Date: Feb. 7, 2019

(65) Prior Publication Data
US 2020/0157150 A1 May 21, 2020

(30) Foreign Application Priority Data
Aug. 1, 2017 (EP) .................................. 17382530

(51) Int. Cl.
*C07K 14/00* (2006.01)
*A61P 35/00* (2006.01)
*A61K 47/51* (2017.01)
*A61K 38/00* (2006.01)

(52) U.S. Cl.
CPC ............ *C07K 14/001* (2013.01); *A61P 35/00* (2018.01); *A61K 38/00* (2013.01); *A61K 47/51* (2017.08); *C07K 2319/00* (2013.01)

(58) Field of Classification Search
None
See application file for complete search history.

(56) References Cited

U.S. PATENT DOCUMENTS

| | | | | |
|---|---|---|---|---|
| 5,512,473 | A * | 4/1996 | Brent .................... | C07K 14/47 435/252.33 |
| 10,639,348 | B2 | 5/2020 | Esteban Martín et al. | |
| 2012/0178700 | A1 * | 7/2012 | Nash ...................... | C07K 14/47 514/19.9 |

FOREIGN PATENT DOCUMENTS

| | | |
|---|---|---|
| WO | 87/06940 A1 | 11/1987 |
| WO | 2010/011313 A2 | 1/2010 |
| WO | 2014/052650 A2 | 4/2014 |
| WO | 2016/164768 A1 | 10/2016 |

OTHER PUBLICATIONS

Altschul et al., "Basic Local Alignment Search Tool," *J. Mol. Biol.* 215:403-410, 1990.
Copolovici et al., "Cell-Penetrating Peptides: Design, Synthesis, and Applications," *ACS Nano* 8(3):1972-1994, 2014.
Edwards et al., "Challenges in Targeting a Basic Helix-Loop-Helix Transcription Factor with Hydrocarbon-Stapled Peptides," *ACS Chem. Biol.* 11:3146-3153, 2016.
Higgins et al., "CLUSTAL V: improved software for multiple sequence alignment," *CABIOS* 8(2):189-191, 1992.
Kim et al., "Synthesis of all-hydrocarbon stapled a-helical peptides by ring-closing olefin metathesis," *Nature Protocols* 6(6):761-771, 2011.
Kolb et al., "The growing impact of click chemistry on drug discovery," *Drug Discovery Today* 8(24):1128-1137, 2003.
Miller et al., "Application of Ring-Closing Metathesis to the Synthesis of Rigidified Amino Acids and Peptides," *J. Am. Chem. Soc.* 118:9606-9614, 1996.

* cited by examiner

*Primary Examiner* — Ronald T Niebauer
(74) *Attorney, Agent, or Firm* — Seed IP Law Group LLP

(57) ABSTRACT

The present invention provides a peptide of formula (I) or a pharmaceutical salt thereof wherein "m", "n", "p", and "q" represent integers and are selected from 0 and 1; and "r" is comprised from 1 to 10; a linker birradical of formula (II), which is connecting an alpha carbon atom of an amino acid located at position "i" in the peptide sequence of formula (I) with an alpha carbon atom of an amino acid located at position "i+4" or "i+7" in the peptide sequence of formula (I); a C-terminal end corresponding to —C(O)R$_4$; and a N-terminal end corresponding to —NHR$_5$. Alternatively, the present invention provides a peptide or a pharmaceutical salt thereof which has an amino acid sequence with an identity from 85% to 95% with respect to sequence SEQ ID NO: 9: The peptides of the invention show anticancer activity. (I)

(I)
—[(Glu)$m$-(Lys)$n$-Ala-Ala-Lys-Val-Val-Ile-Leu-Lys-
Lys-Ala-Thr-Glu-Tyr-Val-(His)$p$-(Ser)$q$]$_r$-

15 Claims, No Drawings

Specification includes a Sequence Listing.

ANTICANCER PEPTIDES

This application claims the benefit of European Patent Application 17382530.8 filed Aug. 1, 2017.

SEQUENCE LISTING

The instant application contains a Sequence Listing that has been submitted electronically in ASCII format and is hereby incorporated by reference in its entirety. Said ASCII copy, created on Dec. 21, 2021, is named 480386_403USPC_SEQUENCE_LISTING, and is 8.5 KB in size.

TECHNICAL FIELD

This invention relates generally to the field of antineoplastic compounds and, more particularly, to the design and synthesis of peptides with improved anticancer activity.

BACKGROUND ART

The therapeutic use of proteins and peptides that act intracellularly holds much promise for the treatment of cancer and other diseases.

Cancer is the result in the occurrence of multiple factors. Mutations may occur in proto-oncogenes that cause cellular proliferation to increase. Mutations also may occur in tumor suppressors whose normal function is to regulate cellular proliferation. Mutations in DNA repair enzymes impair the ability of the cell to repair damage before proliferating.

Tumor suppressor genes are normal genes whose absence (loss or inactivation) can lead to cancer. Tumor suppressor genes encode proteins that slow cell growth and division. Wild-type alleles of tumor suppressor genes express proteins that suppress abnormal cellular proliferation. When the gene coding for a tumor suppressor protein is mutated or deleted, the resulting mutant protein or the complete lack of tumor suppressor protein expression may fail to correctly regulate cellular proliferation, and abnormal cellular proliferation may take place, particularly if there is already existing damage to the cellular regulatory mechanism. A number of well-studied human tumors and tumor cell lines have been shown to have missing or nonfunctional tumor suppressor genes.

Currently, there are few effective options for the treatment of many common cancer types. The course of treatment for a given individual depends on the diagnosis, the stage to which the disease has developed and factors such as age, sex and general health of the patient. The most conventional options of cancer treatment are surgery, radiation therapy and chemotherapy. These therapies each are accompanied with varying side effects and they have varying degrees of efficacy. These side effects, together with the multidrug resistance already disclosed for traditional chemotherapy, have prompted urgent needs for novel anticancer drugs or therapeutic approaches.

Anticancer peptides have become promising molecules for novel anticancer agents because of their unique mechanism and several extraordinary properties. However, properties such as the specificity and sensitivity shown by the peptides already disclosed in the prior art, need further improvement.

Thus, in spite of the efforts made, there is still the need of developing further polypeptides with appropriate anticancer profile.

SUMMARY OF INVENTION

The present inventors found that sequence SEQ ID NO: 1 (hereinafter also referred as "wtN10") was not effective in inhibiting cancer cell proliferation. In an attempt to achieve such anticancer activity, the inventors fused to the N-terminal sequence a cell penetrating peptide (SEQ ID NO: 2, also referred as "intwtN10"), but the resulting peptide was also inactive.

Surprisingly, when said sequence SEQ ID NO: 1 was modified by the inclusion of a side chain bridge (stapling) the peptide sequence became remarkably active in inhibiting cancer cell proliferation (see Table 2 below). The efficiency showed by the peptides of the invention makes that a small amount is required to achieve the desired effect.

Thus, in a first aspect the present invention provides a peptide of formula (I) or a pharmaceutical salt thereof:

$$-[(Glu)m-(Lys)n-Ala-Ala-Lys-Val-Val-Ile-Leu-Lys-Lys-Ala-Thr-Glu-Tyr-Val-(His)p-(Ser)q]_r- \quad (I)$$

wherein

"m", "n", "p", and "q" represent integers and are selected from 0 and 1; and

"r" is comprised from 1 to 10;

the peptide comprising:

a linker birradical "L" of formula (II)

$$-[(R_1)_a-(R_2)-(R_3)_b]_c- \quad (II)$$

which is connecting an alpha carbon atom of an amino acid located at position "i" in the peptide of formula (I) with an alpha carbon atom of an amino acid located at position "i+4" or "i+7" in the peptide of formula (I), a C-terminal end corresponding to $-C(O)R_4$; and a N-terminal end corresponding to $-NHR_5$;

wherein

"a" and "b" are the same or different and are 0 or 1;

"c" is comprised from 1 to 10;

$R_1$ and $R_3$ are birradicals independently selected from the group consisting of: $(C_1-C_{10})$alkyl; $(C_1-C_{10})$alkyl substituted by one or more radicals selected from the group consisting of: halogen, $(C_1-C_{10})$alkyl, $-OR_6$, $-NR_7R_8$, $-SR_9$, $-SOR_{10}$, $-SO_2R_{11}$, and $-CO_2R_{12}$; $(C_2-C_{10})$alkenyl; $(C_2-C_{10})$alkenyl substituted by one or more radicals selected from the group consisting of: halogen, $(C_1-C_{10})$alkyl, $-OR_6$, $-NR_7R_8$, $-SR_9$, $-SOR_{10}$, $-SO_2R_{11}$, and $-CO_2R_{12}$; $(C_2-C_{10})$alkynyl; and $(C_2-C_{10})$alkynyl substituted by one or more radicals selected from the group consisting of: halogen, $(C_1-C_{10})$alkyl, $-OR_6$, $-NR_7R_8$, $-SR_9$, $-SOR_{10}$, $-SO_2R_{11}$, and $-CO_2R_{12}$;

$R_2$ is a birradical selected from the group consisting of: $-O-$, $C(=O)$, $C(=O)NR_{13}$, $C(=O)O$, $S(=O)$, $S(=O)_2$, $NR_{14}$, $(C_1-C_{10})$alkyl, $(C_2-C_{10})$alkenyl, $(C_2-C_{10})$alkynyl, $-NR_{15}-NR_{16}-$, $-N=N-$, $-S-S-$, and a known ring system comprising from 3 to 14 members, the system comprising from 1 to 3 rings, where:

each one of the rings is saturated, partially unsaturated, or aromatic;

the rings are isolated, partially or totally fused, each one of the members forming the known ring system is selected from the group consisting of: $-CH-$, $-CH_2-$, $-NH-$, $-N-$, $-SH-$, $-S-$, and $-O-$; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—; and R$_4$ is a radical selected from the group consisting of —OH and —NR$_{17}$R$_{18}$;

R$_5$ is a radical selected from the group consisting of —H and (C$_1$-C$_{20}$)alkyl;

R$_6$, R$_7$, R$_8$, R$_9$, R$_{10}$, R$_{11}$, R$_{12}$ R$_{13}$, R$_{14}$, R$_{15}$, R$_{16}$, R$_{17}$ and R$_{18}$ are radicals independently selected from the group consisting of: —H and (C$_1$-C$_{10}$)alkyl; and the amino acids, which are connected by the linker, being of formula (III)

wherein

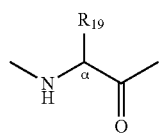

(III)

R$_{19}$ is a monoradical selected from the group consisting of: —H, (C$_1$-C$_{10}$)alkyl, (C$_2$-C$_{10}$)alkenyl, (C$_2$-C$_{10}$)alkynyl, and a known ring system comprising from 3 to 14 members, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—;

or, alternatively, a peptide or a pharmaceutical salt thereof which has an amino acid sequence with an identity from 85% to 95% with respect to sequence SEQ ID NO: 9:

Ala-Ala-X-Val-Val-Ile-Leu-Lys-Lys-X-Thr-Glu-Tyr-Val-His-Ser
         _____L_____/ wherein X and L are as defined above.

In a second aspect the present invention provides a peptide of formula (XI) or a pharmaceutical salt thereof (SEQ ID NO: 13):

(XI)
(Arg)$_m$-(Gln)$_n$-Arg-Arg-Asn-Asp-Leu-Arg-Ser-Ser-Phe-
          Leu-Thr-Leu-Arg-Asp-His-(Val)$_p$-(Pro)$_q$ wherein "m", "n", "p", and "q" represent integers and are selected from 0 and 1; and "r" is comprised from 1 to 10;

the peptide optionally comprising:

a linker birradical "L" of formula (II)

—[(R$_1$)$_a$—(R$_2$)—(R$_3$)$_b$]$_c$— (II)

which is connecting an alpha carbon atom of an amino acid located at position "i" in the peptide of formula (I) with an alpha carbon atom of an amino acid located at position "i+4" or "i+7" in the peptide of formula (I), a C-terminal end corresponding to —C(O)R$_4$; and a N-terminal end corresponding to —NHR$_5$;

wherein

"a" and "b" are the same or different and are 0 or 1;

"c" is comprised from 1 to 10;

R$_1$ and R$_3$ are birradicals independently selected from the group consisting of: (C$_1$-C$_{10}$)alkyl; (C$_1$-C$_{10}$)alkyl substituted by one or more radicals selected from the group consisting of: halogen, (C$_1$-C$_{10}$)alkyl, —OR$_6$, —NR$_7$R$_8$, —SR$_9$, —SOR$_{10}$, —SO$_2$R$_{11}$, and —CO$_2$R$_{12}$; (C$_2$-C$_{10}$)alkenyl; (C$_2$-C$_{10}$)alkenyl substituted by one or more radicals selected from the group consisting of: halogen, (C$_1$-C$_{10}$)alkyl, —OR$_6$, —NR$_7$R$_8$, —SR$_9$, —SOR$_{10}$, —SO$_2$R$_{11}$, and —CO$_2$R$_{12}$; (C$_2$-C$_{10}$)alkynyl; and (C$_2$-C$_{10}$)alkinyl substituted by one or more radicals selected from the group consisting of: halogen, (C$_1$-C$_{10}$)alkyl, —OR$_6$, —NR$_7$R$_8$, —SR$_9$, —SOR$_{10}$, —SO$_2$R$_{11}$, and —CO$_2$R$_{12}$;

R$_2$ is a birradical selected from the group consisting of: —O—, C(=O), C(=O)NR$_{13}$, C(=O)O, S(=O), S(=O)$_2$, NR$_{14}$, (C$_1$-C$_{10}$)alkyl, (C$_2$-C$_{10}$)alkenyl, (C$_2$-C$_{10}$)alkynyl, —NR$_{15}$—NR$_{16}$—, —N=N—, —S—S—, and a known ring system comprising from 3 to 14 members, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—; and R$_4$ is a radical selected from the group consisting of —OH and —NR$_{17}$R$_{18}$;

R$_5$ is a radical selected from the group consisting of —H and (C$_1$-C$_{20}$)alkyl;

R$_6$, R$_7$, R$_8$, R$_9$, R$_{10}$, R$_{11}$, R$_{12}$ R$_{13}$, R$_{14}$, R$_{15}$, R$_{16}$, R$_{17}$ and R$_{18}$ are radicals independently selected from the group consisting of: —H and (C$_1$-C$_{10}$)alkyl; and the amino acids, which are connected by the linker, being of formula (III)

wherein

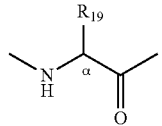

(III)

R$_{19}$ is a monoradical selected from the group consisting of: —H, (C$_1$-C$_{10}$)alkyl, (C$_2$-C$_{10}$)alkenyl, (C$_2$-C$_{10}$)alkynyl, and a known ring system comprising from 3 to 14 members, the system comprising from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—; or, alternatively, a peptide or pharmaceutical salt thereof which has an amino acid sequence with an identity from 85% to 95% with respect to sequence SEQ ID NO: 10, 11 or 12:

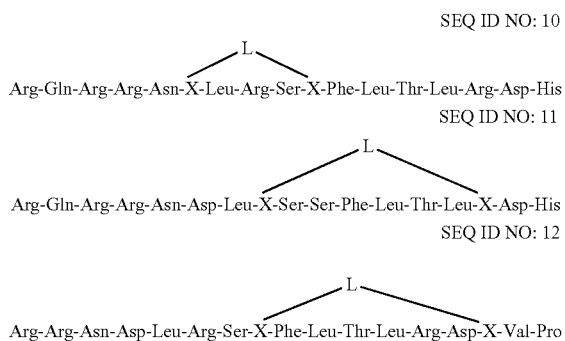

In a third aspect the present invention provides a fusion protein comprising the peptide as defined in the first or second aspect of the invention.

In a fourth aspect, the present invention provides a pharmaceutical composition comprising a therapeutically effective amount of the peptide or pharmaceutical salt thereof as defined in the first or second aspect of the invention, or the fusion protein as defined in the second aspect of the invention, together with acceptable pharmaceutical excipients and/or carriers.

In a fifth aspect, the present invention provides the peptide or pharmaceutical salt thereof as defined in the first or second aspect of the invention or the fusion protein as defined in the third aspect of the invention or the pharmaceutical composition as defined in the fourth aspect of the invention for use as a medicament. This aspect can be alternatively formulated as the use of a peptide or pharmaceutical salt thereof as defined in the first or second aspect of the invention or the fusion protein as defined in the third aspect of the invention, or the pharmaceutical composition as defined in the fourth aspect of the invention, in the manufacture of a medicament for the treatment of a disease. This aspect can also be alternatively formulated as a method for the treatment of a disease, the method comprising administering an effective therapeutic amount of a peptide or pharmaceutical salt thereof as defined in the first or second aspect of the invention or of the fusion protein of the third aspect of the invention or of the pharmaceutical composition as defined in the fourth aspect of the invention, to a subject in need thereof.

In a sixth aspect, the present invention provides the peptide or pharmaceutical salt thereof as defined in the first or second aspect of the invention or the fusion protein as defined in the third aspect of the invention or the pharmaceutical composition as defined in the fourth aspect of the invention for use in the treatment of cancer. This aspect can alternatively be formulated as the use of the peptide or pharmaceutical salt thereof as defined in the first or second aspect of the invention or the fusion protein as defined in the third aspect of the invention or the pharmaceutical composition as defined in the fourth aspect of the invention in the manufacture of a medicament for the treatment of cancer. This aspect can also be alternatively formulated as a method for the treatment of cancer, the method comprising administering an effective therapeutic amount of the peptide or pharmaceutical salt thereof as defined in the first or second aspect of the invention or the fusion protein as defined in the third aspect of the invention or the pharmaceutical composition as defined in the fourth aspect of the invention, to a subject in need thereof.

In further aspects the present invention provides: (a) a combination comprising the peptide or pharmaceutical salt thereof as defined in the first or second aspect of the invention, or the fusion peptide as defined in the third aspect of the invention or the pharmaceutical composition of the fourth aspect of the invention; and a therapeutic agent, particularly an anti-cancer agent; (b) a combination comprising the peptide or pharmaceutical salt thereof as defined in the first or second aspect of the invention, or the fusion peptide of the third aspect of the invention or the pharmaceutical composition of the fourth aspect of the invention; and a therapeutic agent, particularly an anti-cancer agent, for use as a medicament, more particularly for use in the treatment of cancer; (c) a peptide or pharmaceutical salt thereof as defined in the first or second aspect of the invention, or the fusion peptide as defined in the third aspect of the invention, or the pharmaceutical composition as defined in the fourth aspect of the invention for use in combination therapy for the prevention or treatment of cancer, wherein the therapy comprises its administration to a subject simultaneously, sequentially or separately with an anti-cancer agent; and (d) an anti-cancer agent for use in combination therapy with the peptide or pharmaceutical salt thereof as defined in the first or second aspect of the invention, or the fusion peptide as defined in the third aspect of the invention, or the pharmaceutical composition as defined in the fourth aspect of the invention, wherein the use comprises the prevention or treatment of cancer.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

For the purposes of the present invention, any ranges given include both the lower and the upper end-points of the range.

The present invention provides peptides comprising sequences of formula (I) as it has been stated above.

As used herein, the term "pharmaceutical acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutical acceptable salts are well known in the art. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutical acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, and ammonium. Representative alkali or alkaline earth metal salts include sodium, lithium, potassium, calcium, magnesium, and the like. Further pharmaceutical acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The term $(C_1$-$C_{10})$alkyl refers to a saturated straight or branched alkyl chain having from 1 to 10 carbon atoms. Illustrative non-limitative examples are: methyl, ethyl, propyl, isopropyl, butyl, isobutyl, sec-butyl, tert-butyl, n-pentyl, neo-pentyl and n-hexyl.

The term $(C_1$-$C_{20})$alkyl refers to a saturated straight or branched alkyl chain having from 1 to 20 carbon atoms.

The term $(C_2$-$C_{10})$alkenyl refers to a saturated straight, or branched alkyl chain containing from 2 to carbon atoms and also containing one or more double bonds. Illustrative non-limitative examples are ethenyl, propenyl, butenyl, 1-methyl-2-buten-1-yl, and the like.

The term $(C_2$-$C_{10})$alkynyl refers to a saturated straight, or branched alkyl chain containing from 2 to carbon atoms and also containing one or more triple bonds. Examples include, among others, ethynyl, 1-propynyl, 2-butynyl, 1,3-butadinyl, 4-pentynyl, and 1-hexynyl.

The term "halogen" refers to the group in the periodic table consisting of five chemically related elements: fluorine (F), chlorine (Cl), bromine (Br), iodine (I), and astatine (At).

The term $(C_1$-$C_{10})$haloalkyl refers to a group resulting from the replacement of one or more hydrogen atoms from a $(C_1$-$C_{10})$alkyl group with one or more, preferably from 1 to 6, halogen atoms, which can be the same or different. Examples include, among others, trifluoromethyl, fluoromethyl, 1-chloroethyl, 2-chloroethyl, 1-fluoroethyl, 2-fluoroethyl, 2-bromoethyl, 2-iodoethyl, 2,2,2-trifluoroethyl, pentafluoroethyl, 3-fluoropropyl, 3-chloropropyl, 2,2,3,3-tetrafluoropropyl, 2,2,3,3,3-pentafluoropropyl, heptafluoropropyl, 4-fluorobutyl, and nonafluorobutyl.

The term "known" ring system as used herein refers to a ring system which is chemically feasible and is known in the art and so intends to exclude those ring systems that are not chemically possible.

According to the present invention when the ring system is formed by "isolated" rings means that the ring system is formed by two, three or four rings and said rings are bound via a bond from the atom of one ring to the atom of the other ring. The term "isolated" also embraces the embodiment in which the ring system has only one ring. Illustrative non-limitative examples of known ring systems consisting of one ring are those derived from: cyclopropyl, cyclobutyl, cyclopentyl, cyclohexyl, cycloheptyl, cyclopropenyl, cyclobutenyl, cyclopentenyl, phenyl, and cycloheptenyl.

According to the present invention when the ring system has rings "totally fused", means that the ring system is formed by two, three or four rings in which two or more atoms are common to two adjoining rings. Illustrative non-limitative examples are 1,2,3,4-tetrahydronaphthyl, 1-naphthyl, 2-naphthyl, anthryl, or phenanthryl.

According to the present invention when the ring system is "partially fused" it means that the ring system is formed by three or four rings, being at least two of said rings totally fused (i.e. two or more atoms being common to the two adjoining rings) and the remaining ring(s) being bound via a bond from the atom of one ring to the atom of one of the fused rings.

Unless otherwise stated, the amino acids forming the peptides of the invention can have L- or D-configuration.

Amino acids used in the construction of peptides of the present invention may be prepared by organic synthesis, or obtained by other routes, such as, for example, degradation of or isolation from a natural source.

In one embodiment of the first aspect of the invention, optionally in combination with any of the embodiments provided below, r is from 1 to 3. In one embodiment of the first aspect of the invention, optionally in combination with any of the embodiments provided below, r=1. Thus the peptide of the first aspect of the invention consists of the amino acid sequence of formula (I).

In another embodiment of the first aspect of the invention, optionally in combination with any of the embodiments provided above or below, a=1. In another embodiment of the first aspect of the invention, optionally in combination with any of the embodiments provided below, b=1. In another embodiment of the first aspect of the invention, optionally in combination with any of the embodiments provided above or below, c=1. In another embodiment of the first aspect of the invention, optionally in combination with any of the embodiments provided above or below, a=b=c=1. In another embodiment of the first aspect of the invention, optionally in combination with any of the embodiments provided above or below, a=b=c=r=1.

In another embodiment of the first aspect of the invention, optionally in combination with any of the embodiments provided above or below, $R_1$ and $R_3$ are birradicals independently selected from the group consisting of: $(C_1$-$C_{10})$alkyl; $(C_2$-$C_{10})$alkenyl; and $(C_2$-$C_{10})$alkynyl. In another embodiment of the first aspect of the invention, optionally in combination with any of the embodiments provided above or below, $R_1$ and $R_3$ are the same or different and represent $(C_1$-$C_{10})$alkyl.

In another embodiment of the first aspect of the invention, optionally in combination with any of the embodiments provided above or below, $R_2$ is a birradical selected from the group consisting: —O—, C(═O), C(═O)$NR_{13}$, C(═O)O, S(═O), S(═O)$_2$, $NR_{14}$, $(C_1$-$C_{10})$alkyl, $(C_2$-$C_{10})$alkenyl, $(C_2$-$C_{10})$alkynyl, —$NR_{15}$—$NR_{16}$—, —N═N—, —S—S—, and a known ring system consisting of one ring from 3 to 6 members, the ring:
  being saturated, partially unsaturated, or aromatic;
  each one of the members forming the known ring system being selected from the group consisting of: —CH—, —CH$_2$—, —NH—, —N—, —SH—, —S—, and —O—; and
  the ring system being optionally substituted by one or more radicals independently selected from the group consisting of halogen, —OH, —NO$_2$, $(C_1$-$C_{10})$alkyl, $(C_1$-$C_{10})$haloalkyl, and $(C_1$-$C_{10})$alkyl-O—.

In another embodiment of the first aspect of the invention, optionally in combination with any of the embodiments provided above or below, $R_2$ is a birradical selected from the group consisting of: $(C_1$-$C_{10})$alkyl, $(C_2$-$C_{10})$alkenyl, and $(C_2$-$C_{10})$alkynyl. In another embodiment of the first aspect of the invention, optionally in combination with any of the embodiments provided above or below, $R_2$ is $(C_2$-$C_{10})$alkenyl.

In another embodiment of the first aspect of the invention, optionally in combination with any of the embodiments provided above or below, $R_1$ and $R_3$ are the same or different and represent $(C_1$-$C_{10})$alkyl; and $R_2$ is $(C_2$-$C_{10})$alkenyl.

In another embodiment of the first aspect of the invention, optionally in combination with any of the embodiments provided above or below, $R_1$ and $R_3$ are the same or different and represent $(C_1\text{-}C_{10})$alkyl; $R_2$ is $(C_2\text{-}C_{10})$alkenyl; and a=b=c=1.

In another embodiment of the first aspect of the invention, optionally in combination with any of the embodiments provided above or below, $R_1$ and $R_3$ are the same or different and represent $(C_1\text{-}C_{10})$alkyl; $R_2$ is $(C_2\text{-}C_{10})$alkenyl; and r=a=b=c=1.

In another embodiment of the first aspect of the invention, optionally in combination with any of the embodiments In another embodiment of the second aspect of the invention, optionally in combination with any of the embodiments provided above or below, the linker birradical of formula (II) is between an alpha carbon atom of an amino acid located at position "i" in the peptide sequence of formula (I) and an alpha carbon atom of an amino acid located at position "i+7" in the peptide sequence of formula (I).

In another embodiment of the first aspect of the invention, optionally in combination with any of the embodiments provided above or below, the peptide of formula (I) or a pharmaceutical salt thereof is one of formula (Ia):

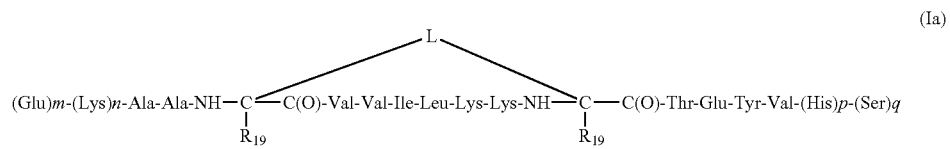

(Ia)

provided above or below, $R_{19}$ is selected from the group consisting of: $(C_1\text{-}C_{10})$alkyl, $(C_2\text{-}C_{10})$alkenyl, and $(C_2\text{-}C_{10})$alkynyl. In another embodiment of the first aspect of the invention, optionally in combination with any of the embodiments provided above or below, $R_{19}$ is a $(C_1\text{-}C_{10})$ alkyl monoradical. In another embodiment of the first aspect of the invention, optionally in combination with any of the embodiments provided above or below, $R_1$, $R_3$ and $R_{19}$ are the same or different and represent $(C_1\text{-}C_{10})$alkyl; and $R_2$ is $(C_2\text{-}C_{10})$alkenyl.

In another embodiment of the first aspect of the invention, optionally in combination with any of the embodiments provided above or below, $R_4$ is —OH (i.e., the C-terminal end is —C(O)OH). In another embodiment of the first aspect of the invention, optionally in combination with any of the embodiments provided above or below, $R_4$ is —$NR_{17}R_{18}$, $R_{17}$ and $R_{18}$ having the same meaning. In another embodiment of the first aspect of the invention, optionally in combination with any of the embodiments provided above or below, $R_4$ is —$NH_2$ (i.e., the C-terminal end is —C(O)$NH_2$).

In another embodiment of the first aspect of the invention, optionally in combination with any of the embodiments provided above or below, the N-terminal end corresponds to —$NH_2$. In another embodiment of the first aspect of the invention, optionally in combination with any of the embodiments provided above or below, the C-terminal and N-terminal ends of the peptide of the invention are, respectively, —C(O)OH and —$NH_2$. In another embodiment of the first aspect of the invention, optionally in combination with any of the embodiments provided above or below, the C-terminal and N-terminal ends of the peptide of the invention are, respectively, —C(O)$NH_2$. and —$NH_2$.

In another embodiment of the first aspect of the invention, optionally in combination with any of the embodiments provided above or below, "m" and "n" means the same (i.e., both are 0 or 1).

In another embodiment of the first aspect of the invention, optionally in combination with any of the embodiments provided above or below, "p" and "q" means the same (i.e., both are 0 or 1).

In another embodiment of the first aspect of the invention, optionally in combination with any of the embodiments provided above or below, "m" and "n" are 1 and "p" and "q" are 0.

wherein "m", "n", "p", "q", L, and $R_{19}$ are as defined above.

In one embodiment of the first aspect of the invention, optionally in combination with any of the embodiments provided above or below, the peptide or pharmaceutical salt thereof is one of formula (Ia). In another embodiment of the first aspect of the invention, optionally in combination with any of the embodiments provided above or below, the peptide or pharmaceutical salt thereof is one of formula (Ia), wherein "m" and "n" are the same. In another embodiment of the first aspect of the invention, optionally in combination with any of the embodiments provided above or below, the peptide or pharmaceutical salt thereof is one of formula (Ia) wherein "m" and "n" are 1. In another embodiment of the first aspect of the invention, optionally in combination with any of the embodiments provided above or below, the peptide or pharmaceutical salt thereof is one of formula (Ia) wherein "p" and "q" are the same. In another embodiment of the first aspect of the invention, optionally in combination with any of the embodiments provided above or below, the peptide or pharmaceutical salt thereof is one of formula (Ia) wherein "p" and "q" are 0. In another embodiment of the first aspect of the invention, optionally in combination with any of the embodiments provided above or below, the peptide or pharmaceutical salt thereof is one of formula (Ia), wherein $R_1$, $R_3$ and $R_{19}$ are the same or different and represent $(C_1\text{-}C_{10})$alkyl; and $R_2$ is $(C_2\text{-}C_{10})$alkenyl. In another embodiment of the first aspect of the invention, optionally in combination with any of the embodiments provided above or below, the peptide or pharmaceutical salt thereof is one of formula (Ia) wherein "m" and "n" are 1, "p" and "q" are 0, $R_1$, $R_3$ and $R_{19}$ are the same or different and represent $(C_1\text{-}C_{10})$alkyl; and $R_2$ is $(C_2\text{-}C_{10})$alkenyl. In another embodiment of the first aspect of the invention, optionally in combination with any of the embodiments provided above or below, the peptide or pharmaceutical salt thereof is one of formula (Ia) wherein "m" and "n" are 1, "p" and "q" are 0, a=b=c=1, $R_1$, $R_3$ and $R_{19}$ are the same or different and represent $(C_1\text{-}C_{10})$alkyl; and $R_2$ is $(C_2\text{-}C_{10})$ alkenyl. In another embodiment of the first aspect of the invention, optionally in combination with any of the embodiments provided above or below, the peptide or pharmaceutical salt thereof is one of formula (Ia) wherein "m" and "n" are 1, "p" and "q" are 0, a=b=c=1, $R_1$, $R_3$ and $R_{19}$ are the same or different and represent $(C_1\text{-}C_{10})$alkyl; and $R_2$ is ($C_2$-$C_{10}$)alkenyl, the C-terminal is selected from —C(O)OH and —$CONH_2$ and the N-terminal end is —$NH_2$.

In another embodiment of the first aspect of the invention, the peptide is of sequence SEQ ID NO: 3:

SEQ ID NO: 3

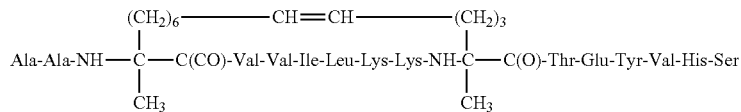

SEQ ID NO: 3 (hereinafter also referred as "NS10")

In an alternative embodiment of the first aspect of the invention, the present invention provides a peptide or a pharmaceutical salt thereof which has an identity from 85% to 95% with the sequence SEQ ID NO: 9, wherein "X" and "L" are as defined in any of the above embodiments. In another alternative embodiment of the first aspect of the invention, the peptide has an identity with respect to sequence SEQ ID NO: 9 of 85, 86, 87, 88, 89, 90, 91, 92, 93, 94 or 95%, and X and L are as defined in any of the above embodiments. In another alternative embodiment of the first aspect of the invention, the peptide has an identity with respect to sequence SEQ ID NO: 9 of 85, 86, 87, 88, 89, 90, 91, 92, 93, 94 or 95%; "L" is a linker biradical wherein "m" and "n" are 1, "p" and "q" are 0, $R_1$ and $R_3$ are the same or different and represent ($C_1$-$C_{10}$)alkyl; and $R_2$ is ($C_2$-$C_{10}$) alkenyl are as defined in any of the above embodiments; and "X" are amino acid residues wherein $R_{19}$ represents ($C_1$-$C_{10}$)alkyl. In another alternative embodiment the peptide has an amino acid sequence with an identity from 85% to 95% with respect sequence SEQ ID NO: 3. In another alternative embodiment of the first aspect of the invention, the peptide has an identity with respect to sequence SEQ ID NO: 9 of 85, 86, 87, 88, 89, 90, 91, 92, 93, 94 or 95%, and X and L are as defined in any of the above embodiments.

In the present invention the term "identity" refers to the percentage of residues or bases that are identical in the two sequences when the sequences are optimally aligned. If, in the optimal alignment, a position in a first sequence is occupied by the same amino acid residue or nucleotide as the corresponding position in the second sequence, the sequences exhibit identity with respect to that position. The level of identity between two sequences (or "percent sequence identity") is measured as a ratio of the number of identical positions shared by the sequences with respect to the size of the sequences (i.e., percent sequence identity= (number of identical positions/total number of positions)× 100). In one embodiment, the two "X" aminoacidic residues connected by the linker, are not considered when performing the alignment to determine the identical positions.

A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, among others. Preferred software analysis programs include the ALIGN, CLUSTAL W, and BLAST programs (e.g., BLAST 2.1, BL2SEQ, and later versions thereof).

For amino acid sequence analysis, a weight matrix, such as the BLOSUM matrixes (e.g., the BLOSUM45, BLOSUM50, BLOSUM62, and BLOSUM80 matrixes), Gonnet matrixes, or PAM matrixes (e.g., the PAM30, PAM70, PAM120, PAM160, PAM250, and PAM350 matrixes), are used in determining identity.

The BLAST programs provide analysis of at least two amino acid sequences, either by aligning a selected sequence against multiple sequences in a database (e.g., GenSeq), or, with BL2SEQ, between two selected sequences. BLAST programs are preferably modified by low complexity filtering programs such as the DUST or SEG programs, which are preferably integrated into the BLAST program operations. If gap existence costs (or gap scores) are used, the gap existence cost preferably is set between about −5 and −15. Similar gap parameters can be used with other programs as appropriate. The BLAST programs and principles underlying them are further described in, e.g., Altschul et al., "Basic local alignment search tool", 1990, J. Mol. Biol, v. 215, pages 403-410.

For multiple sequence analysis, the CLUSTAL W program can be used. The CLUSTAL W program desirably is run using "dynamic" (versus "fast") settings. Amino acid sequences are evaluated using a variable set of BLOSUM matrixes depending on the level of identity between the sequences. The CLUSTAL W program and underlying principles of operation are further described in, e.g., Higgins et al., "CLUSTAL V: improved software for multiple sequence alignment", 1992, CABIOS, 8(2), pages 189-191.

In a second aspect the present invention provides a peptide of formula (XI) or a pharmaceutical salt thereof.

In one embodiment of the second aspect of the invention, optionally in combination with any of the embodiments provided below, r is from 1 to 3. In one embodiment of the second aspect of the invention, optionally in combination with any of the embodiments provided below, r=1. Thus the peptide of the second aspect of the invention consists of the amino acid sequence of formula (XI).

In one embodiment of the second aspect of the invention, optionally in combination with any of the embodiments provided above or below, the peptide or pharmaceutical salt thereof is one of formula (XI), wherein m and n are the same. In one embodiment of the second aspect of the invention, optionally in combination with any of the embodiments provided above or below, the peptide or pharmaceutical salt thereof is one of formula (XI), wherein m and n are 1. In one embodiment of the second aspect of the invention, optionally in combination with any of the embodiments provided above or below, the peptide or pharmaceutical salt thereof is one of formula (XI), wherein p and q are the same. In one embodiment of the second aspect of the invention, optionally in combination with any of the embodiments provided above or below, the peptide or pharmaceutically salt thereof is one of formula (XI), wherein p and q are 0. In another embodiment of the second aspect of the invention, optionally in combination with any of the embodiments provided above or below, the peptide or pharmaceutical salt thereof is of sequence SEQ ID NO: 6:

Arg-Gln-Arg-Arg-Asn-Asp-Leu-Arg-Ser-Ser-Phe-Leu-Thr-Leu-Arg-Asp-His-Val-Pro

In another embodiment of the second aspect of the invention, the peptide comprises a L biradical. In another embodiment of the second aspect of the invention, optionally in combination with any of the embodiments provided above or below, a=1. In another embodiment of the second aspect of the invention, optionally in combination with any of the embodiments provided below, b=1. In another embodiment of the second aspect of the invention, optionally in combination with any of the embodiments provided above or below, c=1. In another embodiment of the second aspect of the invention, optionally in combination with any of the embodiments provided above or below, a=b=c=1. In another embodiment of the second aspect of the invention, optionally in combination with any of the embodiments provided above or below, a=b=c=r=1.

In another embodiment of the second aspect of the invention, optionally in combination with any of the embodiments provided above or below, $R_1$ and $R_3$ are birradicals independently selected from the group consisting of: $(C_1$-$C_{10})$alkyl; $(C_2$-$C_{10})$alkenyl; and $(C_2$-$C_{10})$alkynyl. In another embodiment of the second aspect of the invention, optionally in combination with any of the embodiments provided above or below, $R_1$ and $R_3$ are the same or different and represent $(C_1$-$C_{10})$alkyl.

In another embodiment of the second aspect of the invention, optionally in combination with any of the embodiments provided above or below, $R_2$ is a birradical selected from the group consisting: —O—, C(=O), C(=O)NR$_{13}$, C(=O)O, S(=O), S(=O)$_2$, NR$_{14}$, $(C_1$-$C_{10})$alkyl, $(C_2$-$C_{10})$alkenyl, $(C_2$-$C_{10})$alkynyl, —NR$_{15}$—NR$_{16}$—, —N=N—, —S—S—, and a known ring system consisting of one ring from 3 to 6 members, the ring:

being saturated, partially unsaturated, or aromatic;
each one of the members forming the known ring system being selected from the group consisting of: —CH—, —CH$_2$—, —NH—, —N—, —SH—, —S—, and —O—; and
the ring system being optionally substituted by one or more radicals independently selected from the group consisting of halogen, —OH, —NO$_2$, $(C_1$-$C_{10})$alkyl, $(C_1$-$C_{10})$haloalkyl, and $(C_1$-$C_{10})$alkyl-O—.

In another embodiment of the second aspect of the invention, optionally in combination with any of the embodiments provided above or below, $R_2$ is a birradical selected from the group consisting of: $(C_1$-$C_{10})$alkyl, $(C_2$-$C_{10})$alkenyl, and $(C_2$-$C_{10})$alkynyl. In another embodiment of the second aspect of the invention, optionally in combination with any of the embodiments provided above or below, $R_2$ is $(C_2$-$C_{10})$alkenyl.

In another embodiment of the second aspect of the invention, optionally in combination with any of the embodiments provided above or below, $R_1$ and $R_3$ are the same or different and represent $(C_1$-$C_{10})$alkyl; and $R_2$ is $(C_2$-$C_{10})$alkenyl.

In another embodiment of the second aspect of the invention, optionally in combination with any of the embodiments provided above or below, $R_1$ and $R_3$ are the same or different and represent $(C_1$-$C_{10})$alkyl; $R_2$ is $(C_2$-$C_{10})$alkenyl; and a=b=c=1.

In another embodiment of the second aspect of the invention, optionally in combination with any of the embodiments provided above or below, $R_1$ and $R_3$ are the same or different and represent $(C_1$-$C_{10})$alkyl; $R_2$ is $(C_2$-$C_{10})$alkenyl; and r=a=b=c=1.

In another embodiment of the second aspect of the invention, optionally in combination with any of the embodiments provided above or below, $R_{19}$ is selected from the group consisting of: $(C_1$-$C_{10})$alkyl, $(C_2$-$C_{10})$alkenyl, and $(C_2$-$C_{10})$alkynyl. In another embodiment of the second aspect of the invention, optionally in combination with any of the embodiments provided above or below, $R_{19}$ is a $(C_1$-$C_{10})$alkyl monoradical. In another embodiment of the second aspect of the invention, optionally in combination with any of the embodiments provided above or below, $R_1$, $R_3$ and $R_{19}$ are the same or different and represent $(C_1$-$C_{10})$alkyl; and $R_2$ is $(C_2$-$C_{10})$alkenyl.

In another embodiment of the second aspect of the invention, optionally in combination with any of the embodiments provided above or below, $R_4$ is —OH (i.e., the C-terminal end is —C(O)OH). In another embodiment of the second aspect of the invention, optionally in combination with any of the embodiments provided above or below, $R_4$ is —NR$_{17}$R$_{18}$, R$_{17}$ and R$_{18}$ having the same meaning. In another embodiment of the second aspect of the invention, optionally in combination with any of the embodiments provided above or below, $R_4$ is —NH$_2$ (i.e., the C-terminal end is —C(O)NH$_2$).

In another embodiment of the second aspect of the invention, optionally in combination with any of the embodiments provided above or below, the N-terminal end corresponds to —NH$_2$. In another embodiment of the second aspect of the invention, optionally in combination with any of the embodiments provided above or below, the C-terminal and N-terminal ends of the peptide of the invention are, respectively, —C(O)OH and —NH$_2$. In another embodiment of the second aspect of the invention, optionally in combination with any of the embodiments provided above or below, the C-terminal and N-terminal ends of the peptide of the invention are, respectively, —C(O)NH$_2$. and —NH$_2$.

In another embodiment of the second aspect of the invention, optionally in combination with any of the embodiments provided above or below, "m" and "n" means the same (i.e., both are 0 or 1).

In another embodiment of the second aspect of the invention, optionally in combination with any of the embodiments provided above or below, "p" and "q" means the same (i.e., both are 0 or 1).

In another embodiment of the second aspect of the invention, optionally in combination with any of the embodiments provided above or below, "m" and "n" are 1 and "p" and "q" are 0.

In another embodiment of the second aspect of the invention, optionally in combination with any of the embodiments provided above or below, the peptide of formula (XI) or a pharmaceutical salt thereof is one of formula (XIa), (XIb) or (XIc):

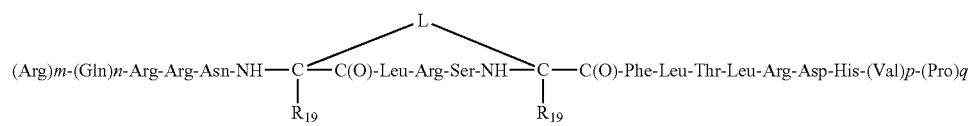

XIa

-continued $$\text{(Arg)}m\text{-(Gln)}n\text{-Arg-Arg-Asn-Asp-Leu-NH} - \underset{R_{19}}{\overset{L}{C}} C(O)\text{-Ser-Ser-Phe-Leu-Thr-Leu-NH} - \underset{R_{19}}{\overset{}{C}} - C(O)\text{-Asp-His-(Val)}p\text{-(Pro)}q \quad \text{XIb}$$

$$\text{(Arg)}m\text{-(Gln)}n\text{-Arg-Arg-Asn-Asp-Leu-Arg-Ser-NH} - \underset{R_{19}}{\overset{L}{C}} C(O)\text{-Phe-Leu-Thr-Leu-Arg-Asp-NH} - \underset{R_{19}}{\overset{}{C}} - C(O)\text{-(Val)}p\text{-(Pro)}q \quad \text{XIc}$$

wherein "m", "n", "p", "q", L, and $R_{19}$ are as defined in any of the above embodiments.

In one embodiment of the second aspect of the invention, optionally in combination with any of the embodiments provided above or below, the peptide or pharmaceutical salt thereof is one of formula (XIa). In another embodiment of the second aspect of the invention, optionally in combination with any of the embodiments provided above or below, the peptide or pharmaceutical salt thereof is one of formula (XIa), wherein "m" and "n" are the same. In another embodiment of the second aspect of the invention, optionally in combination with any of the embodiments provided above or below, the peptide or pharmaceutical salt thereof is one of formula (XIa) wherein "m" and "n" are 1. In another embodiment of the second aspect of the invention, optionally in combination with any of the embodiments provided above or below, the peptide or pharmaceutical salt thereof is one of formula (XIa) wherein "p" and "q" are the same. In another embodiment of the second aspect of the invention, optionally in combination with any of the embodiments provided above or below, the peptide or pharmaceutical salt thereof is one of formula (XIa) wherein "p" and "q" are 0. In another embodiment of the second aspect of the invention, optionally in combination with any of the embodiments provided above or below, the peptide or pharmaceutical salt thereof is one of formula (XIa), wherein $R_1$, $R_3$ and $R_{19}$ are the same or different and represent $(C_1\text{-}C_{10})$alkyl; and $R_2$ is $(C_2\text{-}C_{10})$alkenyl. In another embodiment of the second aspect of the invention, optionally in combination with any of the embodiments provided above or below, the peptide or pharmaceutical salt thereof is one of formula (XIa) wherein "m" and "n" are 1, "p" and "q" are 0, $R_1$, $R_3$ and $R_{19}$ are the same or different and represent $(C_1\text{-}C_{10})$alkyl; and $R_2$ is $(C_2\text{-}C_{10})$alkenyl. In another embodiment of the second aspect of the invention, optionally in combination with any of the embodiments provided above or below, the peptide or pharmaceutical salt thereof is one of formula (XIa) wherein "m" and "n" are 1, "p" and "q" are 0, a=b=c=1, $R_1$, $R_3$ and $R_{19}$ are the same or different and represent $(C_1\text{-}C_{10})$alkyl; and $R_2$ is $(C_2\text{-}C_{10})$alkenyl. In another embodiment of the first aspect of the invention, optionally in combination with any of the embodiments provided above or below, the peptide or pharmaceutical salt thereof is one of formula (XIa) wherein "m" and "n" are 1, "p" and "q" are 0, a=b=c=1, $R_1$, $R_3$ and $R_{19}$ are the same or different and represent $(C_1\text{-}C_{10})$alkyl; and $R_2$ is $(C_2\text{-}C_{10})$alkenyl, the C-terminal is selected from —C(O)OH and —CONH$_2$ and the N-terminal end is —NH$_2$.

In another embodiment of the second aspect of the invention, optionally in combination with any of the embodiments provided above or below, the peptide or pharmaceutical salt thereof is one of formula (XIb). In another embodiment of the second aspect of the invention, optionally in combination with any of the embodiments provided above or below, the peptide or pharmaceutical salt thereof is one of formula (XIb), wherein "m" and "n" are the same. In another embodiment of the second aspect of the invention, optionally in combination with any of the embodiments provided above or below, the peptide or pharmaceutical salt thereof is one of formula (XIb) wherein "p" and "q" are the same. In another embodiment of the second aspect of the invention, optionally in combination with any of the embodiments provided above or below, the peptide or pharmaceutical salt thereof is one of formula (XIb), wherein $R_1$, $R_3$ and $R_{19}$ are the same or different and represent $(C_1\text{-}C_{10})$alkyl; and $R_2$ is $(C_2\text{-}C_{10})$alkenyl. In another embodiment of the second aspect of the invention, optionally in combination with any of the embodiments provided above or below, the peptide or pharmaceutical salt thereof is one of formula (Ia) wherein "m" and "n" are 1, "p" and "q" are 0, $R_1$, $R_3$ and $R_{19}$ are the same or different and represent $(C_1\text{-}C_{10})$ alkyl; and $R_2$ is $(C_2\text{-}C_{10})$alkenyl. In another embodiment of the second aspect of the invention, optionally in combination with any of the embodiments provided above or below, the peptide or pharmaceutical salt thereof is one of formula (XIb) wherein "m" and "n" are 1, "p" and "q" are 0, a=b=c=1, $R_1$, $R_3$ and $R_1$ are the same or different and represent $(C_1\text{-}C_{10})$alkyl; and $R_2$ is $(C_2\text{-}C_{10})$alkenyl. In another embodiment of the first aspect of the invention, optionally in combination with any of the embodiments provided above or below, the peptide or pharmaceutical salt thereof is one of formula (Ia) wherein "m" and "n" are 1, "p" and "q" are 0, a=b=c=1, $R_1$, $R_3$ and $R_{19}$ are the same or different and represent $(C_1\text{-}C_{10})$alkyl; and $R_2$ is $(C_2\text{-}C_{10})$ alkenyl, the C-terminal is selected from —C(O)OH and —CONH$_2$ and the N-terminal end is —NH$_2$.

In one embodiment of the second aspect of the invention, optionally in combination with any of the embodiments provided above or below, the peptide or pharmaceutical salt thereof is one of formula (XIc). In another embodiment of the second aspect of the invention, optionally in combination with any of the embodiments provided above or below, the peptide or pharmaceutical salt thereof is one of formula (XIc), wherein "m" and "n" are the same. In another embodiment of the second aspect of the invention, optionally in combination with any of the embodiments provided above or below, the peptide or pharmaceutical salt thereof is one of formula (XIc) wherein "m" and "n" are 0. In another embodiment of the second aspect of the invention, optionally in combination with any of the embodiments provided above or below, the peptide or pharmaceutical salt thereof is one of formula (XIc) wherein "p" and "q" are the same. In another embodiment of the second aspect of the invention, optionally in combination with any of the embodiments provided above or below, the peptide or pharmaceutical salt thereof is one of formula (XIc) wherein "p" and "q" are 1. In another embodiment of the second aspect of the invention, optionally in combination with any of the embodiments provided above or below, the peptide or pharmaceutical salt thereof is one of formula (XIc), wherein $R_1$, $R_3$ and $R_{19}$ are the same or different and represent $(C_1-C_{10})$alkyl; and $R_2$ is $(C_2-C_{10})$alkenyl. In another embodiment of the second aspect of the invention, optionally in combination with any of the embodiments provided above or below, the peptide or pharmaceutical salt thereof is one of formula (XIc) wherein "m" and "n" are 0, "p" and "q" are 1, $R_1$, $R_3$ and $R_{19}$ are the same or different and represent $(C_1-C_{10})$alkyl; and $R_2$ is $(C_2-C_{10})$alkenyl. In another embodiment of the second aspect of the invention, optionally in combination with any of the embodiments provided above or below, the peptide or pharmaceutical salt thereof is one of formula (XIc) wherein "m" and "n" are 0, "p" and "q" are 1, a=b=c=1, $R_1$, $R_3$ and $R_{19}$ are the same or different and represent $(C_1-C_{10})$alkyl; and $R_2$ is $(C_2-C_{10})$alkenyl. In another embodiment of the first aspect of the invention, optionally in combination with any of the embodiments provided above or below, the peptide or pharmaceutical salt thereof is one of formula (XIc) wherein "m" and "n" are 0, "p" and "q" are 1, a=b=c=1, $R_1$, $R_3$ and $R_{19}$ are the same or different and represent $(C_1-C_{10})$alkyl; and $R_2$ is $(C_2-C_{10})$alkenyl, the C-terminal is selected from —C(O)OH and —CONH$_2$ and the N-terminal end is —NH$_2$.

In another embodiment of the second aspect of the invention, the peptide is selected from the group consisting of SEQ ID NO: 4, 5 and 7:

the above embodiments. In another alternative embodiment of the first aspect of the invention, the peptide has an identity with respect to sequence SEQ ID NO: 10, 11 or 12 of 85, 86, 87, 88, 89, 90, 91, 92, 93, 94 or 95%; "L" is a linker biradical wherein "m" and "n" are 1, "p" and "q" are 0, $R_1$ and $R_3$ are the same or different and represent $(C_1-C_{10})$alkyl; and $R_2$ is $(C_2-C_{10})$alkenyl are as defined in any of the above embodiments; and "X" are amino acid residues wherein $R_{19}$ represents $(C_1-C_{10})$alkyl. In another alternative embodiment the peptide has an amino acid sequence with an identity from 85% to 95% with respect to sequence SEQ ID NO: 4, 5 or 7. In another alternative embodiment of the first aspect of the invention, the peptide has an identity of 85, 86, 87, 88, 89, 90, 91, 92, 93, 94 or 95% with respect to sequence SEQ ID NO: 4, 5 or 7.

In one embodiment, the two "X" amino acidic residues connected by the linker are not considered when performing the alignment with the sequence SEQ ID NO: 4, 5, 7, 10, 11 or 12 to determine the identical positions.

In one embodiment, the peptide of the first or second aspect of the invention is conjugated to a label. In one embodiment, the label is conjugated to the N-terminal of the peptide.

A "label" as used herein is a molecule or compound that can be detected by a variety of methods including fluorescence, electrical conductivity, radioactivity, size, and the like. The label may be intrinsically capable of emitting a signal, such as for example fluorescent label that emits light of a particular wavelength following excitation by light of another lower, characteristic wavelength. Alternatively, the label may not be capable of intrinsically emitting a signal but

SEQ ID NO: 4

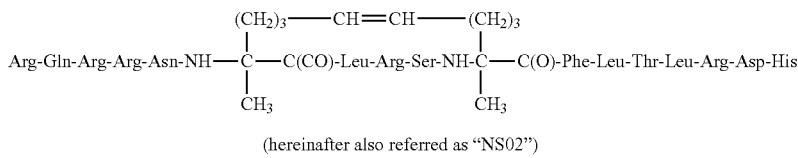

(hereinafter also referred as "NS02")

SEQ ID NO: 5

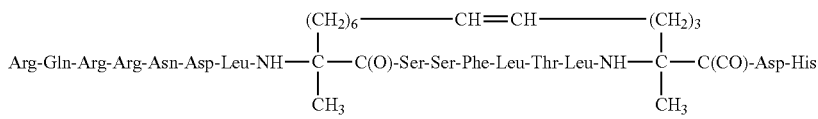

(hereinafter also referred as "NS16")

SEQ ID NO: 7

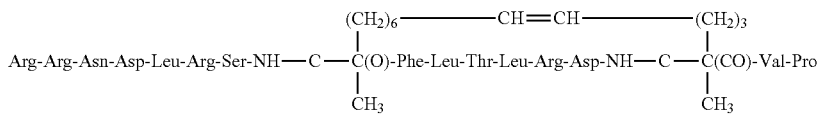

(hereinafter also referred as "Na05")

In an alternative embodiment, of the second aspect of the invention, the present invention provides a peptide or a pharmaceutical salt thereof which has an identity from 85% to 95% with the sequence SEQ ID NO: 10, 11 or 12, wherein "X" and "L" are as defined in any of the above embodiments. In another alternative embodiment of the first aspect of the invention, the peptide has an identity with respect to sequence SEQ ID NO: 10, 11 or 12 of 85, 86, 87, 88, 89, 90, 91, 92, 93, 94 or 95%, and X and L are as defined in any of it may be capable of being bound by another compound that does emit a signal. An example of this latter situation is a label such as biotin which itself does not emit a signal but which when bound to labeled avidin or streptavidin molecules can be detected. Other examples of this latter kind of label are ligands that bind specifically to particular receptors. Detectably labeled receptors are allowed to bind to ligand labeled unit specific markers in order to visualize such markers.

Labels that may be used according to the invention include but are not limited to electron spin resonance molecule, a fluorescent molecule, a chemiluminescent molecule, a radioisotope, an enzyme substrate, an enzyme, a biotin molecule, an avidin molecule, an electrical charge transferring molecule, a semiconductor nanocrystal, a semiconductor nanoparticle, a colloid gold nanocrystal, a ligand, a microbead, a magnetic bead, a paramagnetic molecule, a quantum dot, a chromogenic substrate, an affinity molecule, a protein, a peptide, nucleic acid, a carbohydrate, a hapten, an antigen, an antibody, an antibody fragment, and a lipid.

Radioisotopes can be detected with film or charge coupled devices (CCDs), ligands can be detected by binding of a receptor having a fluorescent, chemiluminescent or enzyme tag, and microbeads can be detected using electron or atomic force microscopy.

The conjugation of the label to the peptide can be performed following routine protocols well-known for the skilled in the art.

In another embodiment, the peptide of the first or second aspect of the invention is conjugated to a drug. In one embodiment, the drug is conjugated to the N-terminal end of the peptide.

The process for the preparation of the peptides according to the first or second aspect of the invention comprises:

(1.a) the coupling, by condensation, of the corresponding amino acids of the peptide with a compound of formula (IV) and a compound of formula (V), which correspond to the amino acids referred as "i" and "i+4" or "i+7". Compounds (IV) and (V) will be those suffering a subsequent cyclization step to generate the "L" birradical":

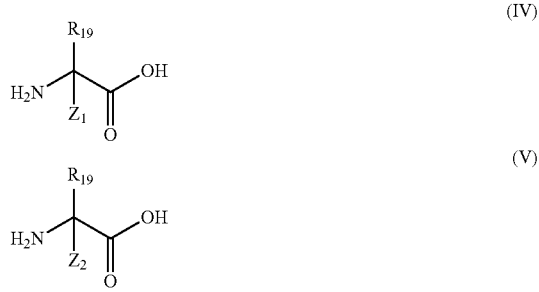

wherein $R_{19}$ is as defined above, $Z_1$ and $Z_2$ are the same or different and represent $(C_2-C_{10})$alkenyl; and (1.b) a cyclization step comprising the ring-closed metathesis of $Z_1$ and $Z_2$ (cf. Kim Young-Woo et al., "Synthesis of all-hydrocarbon stapled a-helical peptides by ring-closing olefin metathesis", Nature Protocols, 2011, 6(6), p. 761-771; Scott J. M. et al., "Application of Ring-Closing Metathesis to the Synthesis of Rigidified Amino Acids and Peptides", J. Am. Chem. Soc., 1996, v.118 (40), pp 9606-9614) performed in solution with a Grubbs (I or II generation) catalyst; or, alternatively, (2a) the coupling, by condensation, of the required amino acids, including a compound of formula (VI) and a compound of formula (VII), which correspond to the amino acids referred as "i" and "i+4" or "i+7". Compounds (VI) and (VII) will be those suffering a subsequent cyclization step to generate the "L" birradical":

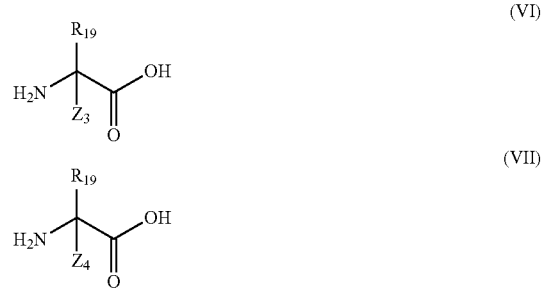

wherein $R_{19}$ is as defined above, $Z_3$ and $Z_4$ are the same or different, selected from the group consisting of: halogen —SH, —NHR$_{20}$, —OH, $(C_2-C_{10})$alkyl-SH, $(C_1-C_{10})$alkyl-OH, $(C_1-C_{10})$alkyl-NHR$_{21}$, C(=O)OH, $(C_1-C_{10})$C(=O)OH, C(=O)NHR$_{22}$, $(C_1-C_{10})$alkylC(=O)NHR$_{23}$, OR$_{24}$, C(=O)-halogen, C(=O)—OR$_{25}$, S(=O)-halogen, S(=O)—OR$_{26}$, S(=O)$_2$R$_{27}$ where R$_{20}$, R$_{21}$ R$_{22}$, R$_{23}$, R$_{24}$, R$_{25}$ R$_{26}$ and R$_{27}$ are monoradicals selected from the group consisting of: hydrogen, $(C_1-C_{10})$alkyl, $(C_2-C_{10})$alkenyl, and $(C_2-C_{10})$alkinyl; a known ring system comprising from 3 to 14 carbon atoms, the system comprising from 1 to 3 rings, where:

each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NH$_2$, —SH, C(=O)-halogen $(C_1-C_{10})$haloalkyl, and $(C_1-C_{10})$alkyl-O—; and (2b) a cyclization step comprising the coupling reaction between $Z_3$ and $Z_4$ radicals; or, alternatively, (3a) the coupling, by condensation, of the corresponding amino acids of the peptide with a compound of formula (VIII) and a compound of formula (IX), which correspond to the amino acids referred as "i" and "i+4" or "i+7". Compounds (VIII) and (IX) will be those suffering a subsequent cyclization step to generate the "L" birradical":

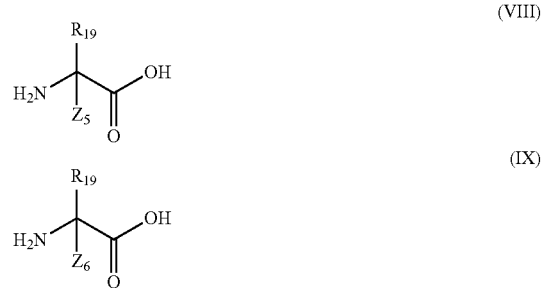

wherein $R_{19}$ is as defined above, one of $Z_5$ and $Z_6$ is $(C_2-C_{10})$alkynyl and the other is $(C_2-C_{10})$alkylN$_3$; and (3.b) a cyclization step comprising the condensation of $Z_5$ and $Z_6$ radicals by well-known protocols such as the Cu(I)-mediated Huisgen 1,3-dipolar cycloaddition reaction (a.k.a. a "click" reaction) to generate a 1,4-substituted 1,2,3-triazole bridge (cf. Kolb H. C. et al., "The growing impact of click chemistry on drug discovery", 2003, Drug Discov Today, 8(24):1128-1137).

The process for the preparation of the peptide according to the second aspect of the invention comprises the coupling, by condensation, of the carboxylic group or C-terminus of one amino acid with the amino group or N-terminus of another, this coupling reaction being repeated the number of times required until the desired peptide is obtained.

The compounds of formula (IV), (V), (VI), (VII), (VIII), and (IX) are commercially available and are coupled by condensation to the already formed portion of peptide sequence. These compounds can carry beads for the appropriate solid phase synthesis of the peptide, as well as protecting groups of the carboxy, amino or side-chain. Illustrative non-limitative examples of compounds are: 2-(2'-propenyl)alanine, 2-(3'-butenyl)glycine, 2-(4'-pentenyl)alanine, 2-(6'-heptenyl) alanine, 2-(7'-octenyl)alanine, and allyl-glycine, 5-azido-norvaline, alpha-propargyl-alanine, among others.

The "coupling" step can be performed in solid phase, following the protocol "deprotection-wash-coupling-wash", by condensation of the carboxylic group of one amino acid with the amino group of another amino acid residue, using amino acids as defined above as well as alpha-alpha di-substituted amino acids of formula (IV) to (IX) in the order of interest to obtain the desired peptide.

The general principle of solid phase peptide synthesis is to repeat cycles of deprotection-wash-coupling-wash. The free N-terminal amine of a solid-phase attached peptide is coupled to a single N-protected amino acid unit. This unit is then deprotected, revealing a new N-terminal amine to which a further amino acid may be attached. Amino acids have reactive moieties at the N- and C-termini, which facilitates amino acid coupling during synthesis. Many amino acids also have reactive side chain functional groups, which can interact with free termini or other side chain groups during synthesis and peptide elongation and negatively influence yield and purity. To facilitate proper amino acid synthesis with minimal side chain reactivity, chemical groups have been developed to bind to specific amino acid functional groups and block, or protect, the functional group from nonspecific reactions. These protecting groups, while vast in nature, can be separated into three groups, as follows: N-terminal protecting groups, C-terminal protecting groups (mostly used in liquid-phase synthesis), and side chain protecting groups.

For coupling the peptides the carboxyl group is usually activated. This is important for speeding up the reaction. There are two main types of activating groups: carbodiimides and triazolols. However, the use of pentafluorophenyl esters (FDPP, PFPOH]) and BOP-Cl are useful for cyclising peptides.

Purified, individual amino acids are reacted with these protecting groups prior to synthesis and then selectively removed during specific steps of peptide synthesis.

Exemplary resins which may be employed by the present invention include, but are not limited to: (1) alkenyl resins (e.g., REM resin, vinyl sulfone polymer-bound resin, vinylpolystyrene resin); (2) amine functionalized resins (e.g., amidine resin, N-(4-Benzyloxybenzyl)hydroxylamine polymer bound, (aminomethyl)polystyrene, polymer bound (R)-(+)-a-methylbenzylamine, 2-Chlorotrityl Knorr resin, 2-N-Fmoc-Amino-dibenzocyclohepta-1,4-diene, polymer-bound resin, 4-[4-(1-Fmoc-aminoethyl)-2-methoxy-5-nitrophenoxy]butyramidomethyl-polystyrene resin, 4-Benzyloxybenzylamine, polymer-bound, 4-Carboxybenzenesulfonamide, polymer-bound, Bis(tert-butoxycarbonyl)thiopseudourea, polymer-bound, Dimethylaminomethyl-polystyrene, Fmoc-3-amino-3-(2-nitrophenyl)propionic acid, polymer-bound, N-Methyl aminomethylated polystyrene, PAL resin, Sieber amide resin, tert-Butyl N-(2-mercaptoethyl)carbamate, polymer-bound, Triphenylchloromethane-4-carboxamide polymer bound); (3) benzhydrylamine (BHA) resins (e.g., 2-Chlorobenzhydryl chloride, polymer-bound, HMPB-benzhydrylamine polymer bound, 4-Methylbenzhydrol, polymer-bound, Benzhydryl chloride, polymer-bound, Benzhydrylamine polymer-bound); (4) Br-functionalized resins (e.g., 4-(Benzyloxy)benzyl bromide polymer bound, 4-Bromopolystyrene, Brominated PPOA resin, Brominated Wang resin, Bromoacetal, polymer-bound, Bromopolystyrene, HypoGel® 200 Br, Polystyrene A-Br for peptide synthesis, Selenium bromide, polymer-bound, TentaGel HL-Br, TentaGel MB-Br, TentaGel S-Br, TentaGel S-Br); (5) Chloromethyl resins (e.g., 5-[4-(Chloromethyl)phenyl]pentyl]styrene, polymer-bound, 4-(Benzyloxy)benzyl chloride polymer bound, 4-Methoxybenzhydryl chloride, polymer-bound); (6) CHO-functionalized resins (e.g., (4-Formyl-3-methoxyphenoxymethyl)polystyrene, (4-Formyl-3-methoxyphenoxymethyl)polystyrene, 3-Benzyloxybenzaldehyde, polymer-bound, 4-Benzyloxy-2,6-dimethoxybenzaldehyde, polymer-bound, Formylpolystyrene, HypoGel® 200 CHO, Indole resin, Polystyrene A—CH(OEt)2, TentaGel HL—CH(OEt)2); (7) Cl-functionalized resins (e.g., Benzoyl chloride polymer bound, (chloromethyl)polystyrene, Merrifield's resin); N(8) CO2H functionalized resins (e.g., Carboxyethylpolystryrene, HypoGel® 200 COOH, Polystyrene AM—COOH, TentaGel HL—COOH, TentaGel MB—COOH, TentaGel S—COOH); (9) Hypo-Gel resins (e.g., HypoGel® 200 FMP, HypoGel® 200 PHB, HypoGel® 200 Trt-OH, HypoGel® 200 HMB); (10) I-functionalized resins (e.g., 4-Iodophenol, polymer-bound, Iodopolystyrene); Janda-Jes™ (JandaJel<ä>-Rink amide, JandaJel-NH2, JandaJel—Cl, JandaJel-4-Mercaptophenol, JandaJel-OH, JandaJel-1-(3-Dimethylaminopropyl)-3-ethylcarbodiimide, JandaJel-1,3,4,6,7,8-hexahydro-2H-pyrimido-[1,2-a]pyrimidine, JandaJel-morpholine, JandaJel-polypyridine, JandaJel-Triphenylphosphine, JandaJel-Wang); (11) MBHA resins (3[4'-(Hydroxymethyl)phenoxy]propionic acid-4-methylbenzhydrylamine resin, 4-(Hydroxymethyl)phenoxyacetic acid polymer-bound to MBHA resin, HMBA-4-methylbenzhydrylamine polymer bound, 4-Methylbenzhydrylamine hydrochloride polymer bound Capacity (amine)); (12) NH2 functionalized resins ((Aminomethyl)polystyrene, (Aminomethyl)polystyrene, HypoGel® 200 NH2, Polystyrene AM-NH2, Polystyrene Microspheres 2-aminoethylated, Polystyrol Microspheres 2-bromoethylated, Polystyrol Microspheres 2-hydroxyethylated, TentaGel HL-NH2, Tentagel M Br, Tentagel M NH2, Tentagel M OH, TentaGel MB-NH2, TentaGel S—NH2, TentaGel S—NH2); (13) OH-functionalized resins (e.g., 4-hydroxymethylbenzoic acid, polymer-bound, Hydroxymethyl Resins, OH-functionalized Wang Resins); (14) oxime resins (e.g., 4-Chlorobenzophenone oxime polymer bound, Benzophenone oxime polymer bound, 4-Methoxybenzophenone oxime polymer bound); (15) PEG resins (e.g., ethylene glycol polymer bound); (16) Boc-/Blz peptide synthesis resins (e.g., Boc-Lys(Boc)-Lys[Boc-Lys(Boc)]-Cys(Acm)-b-Ala-O-PAM resin, Boc-Lys(Fmoc)-Lys[Boc-Lys(Fmoc)]-b-Ala-O-Pam resin, Boc-Lys(Boc)-Lys[Boc-Lys(Boc)]-Lys{Boc-Lys(Boc)-Lys[Boc-Lys(Boc)]}-b-Ala-O-PAM resin, Boc-Lys(Fmoc)-Lys[Boc-Lys(Fmoc)]-Lys[Boc-Lys(Fmoc)-Lys{Boc-Lys(Fmoc)]}-b-Ala-O-PAM resin, Boc- Lys(Boc)-Lys[Boc-Lys(Boc)]-Lys{Boc-Lys(Boc)-Lys[Boc-Lys(Boc)]}-Cys(Acm)-b-Ala-O-PAM resin, Preloaded PAM resins); (17) Fmoc-/t-Bu peptide synthesis resins (e.g., Fmoc-Lys(Fmoc)-Lys[Fmoc-Lys(Fmoc)]-b-Ala-O-Wang resin, Fmoc-Lys(Fmoc)-Lys[Fmoc-Lys(Fmoc)]-Lys{Fmoc-Lys(Fmoc)-Lys[Fmoc-Lys(Fmoc)]}-b-Ala-O-Wang resin, Preloaded TentaGel® S Trityl Resins, Preloaded TentaGel® Resins, Preloaded Trityl Resins, Preloaded Wang Resins, Trityl Resins Preloaded with Amino Alcohols); (19) thiol-functionalized resins (e.g., HypoGel® 200 S-Trt, Polystyrene AM-S-Trityl, TentaGel HL-S-Trityl, TentaGel MB-S-Trityl, TentaGel S-S-Trityl); and (20) Wang resins (e.g., Fmoc-Ala-Wang resin, Fmoc-Arg(Pbf)-Wang resin, Fmoc-Arg(Pmc)-Wang resin, Fmoc-Asn(Trt)-Wang resin, Fmoc-Asp(OtBu)-Wang resin, Fmoc-Cys(Acm)-Wang resin, Fmoc-Cys(StBu)-Wang resin, Fmoc-Cys(Trt) Wang resin, Fmoc-Gln(Trt)-Wang resin, Fmoc-Glu(OtBu)-Wang resin, Fmoc-Gly-Wang resin, Fmoc-His(Trt)-Wang resin, Fmoc-Ile-Wang resin, Fmoc-Leu-Wang resin, Fmoc-Lys(Boc)-Wang resin, Fmoc-Met-Wang resin, Fmoc-D-Met-Wang resin, Fmoc-Phe-Wang resin, Fmoc-Pro-Wang resin, Fmoc-Ser(tBu)-Wang resin, Fmoc-Ser(Trt)-Wang resin, Fmoc-Thr (tBu)-Wang resin, Fmoc-Trp(Boc) Wang resin, Fmoc-Trp-Wang resin, Fmoc-Tyr(tBu)-Wang resin, Fmoc-Val-Wang resin).

"Protecting group" (PG) refers to a grouping of atoms that when attached to a reactive group in a molecule masks, reduces or prevents that reactivity.

Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, Ntriphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

In a third aspect, the present invention provides a fusion peptide comprising the peptide as defined in the first or second aspect of the invention, or in any of the embodiments of the first or second aspect of the invention, and a cell penetrating peptide.

In the present invention the term "cell penetrating peptide" ("CPP") refers to short peptides that facilitate cellular uptake of various molecular cargo (from nanosize particles to small chemical molecules and large fragments of DNA). The "cargo" is associated to peptides via the C(t) or N(t)-end, either through chemical linkage via covalent bonds or through non-covalent interactions. The function of the CPPs are to deliver the cargo into cells, a process that commonly occurs through endocytosis with the cargo delivered to delivery vectors for use in research and medicine. Current use is limited by a lack of cell specificity in CPP-mediated cargo delivery and insufficient understanding of the modes of their uptake. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. The conjugation of the CPP to the peptide provided in the present invention can be performed following well-known routine protocols, such as solid phase synthesis or solution selective capping. (cf. Copolovici D. M. et al., "Cell-Penetrating Peptides: Design, Synthesis, and Applications", 2014, ACS Nano, 2014, 8 (3), pp 1972-1994).

In another embodiment of the third aspect of the invention, provided above or below, the cell penetrating peptide is a polycationic CPP. In another embodiment of the third aspect of the invention, optionally in combination with any of the embodiments provided above or below, the cell penetrating peptide is polyArg or, alternatively penetratine.

In another embodiment of the third aspect of the invention, the fusion peptide is one of sequence SEQ ID NO: 8 (hereinafter also referred as "NLCa02"):

Arg-Gln-Ile-Lys-Ile-Trp-Phe-Gln-Asn-Arg-Arg-Met-Lys-Trp-Lys-Lys-Arg-Gln-Arg-Arg-Asn-Asp-Leu-Arg-Ser-Ser-Phe-Leu-Thr-Leu-Arg-Asp-His-Val-Pro

In a fourth aspect the present invention provides a pharmaceutical composition.

The expression "therapeutically effective amount" as used herein, refers to the amount of a compound that, when administered, is sufficient to prevent development of, or alleviate to some extent, one or more of the symptoms of the disease which is addressed. The particular dose of the peptide administered according to this invention will of course be determined by the particular circumstances surrounding the case, including the compound administered, the route of administration, the particular condition being treated, and the similar considerations.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio. Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The formulations of the pharmaceutical compositions described herein may be prepared by any method known or hereafter developed in the art of pharmacology. In general, such preparatory methods include the step of bringing the active ingredient (the peptide) into association with a excipient and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient (i.e., the peptide as defined in any of the previous aspects and embodiments), the pharmaceutically acceptable excipient, and/or any additional ingredients in a pharmaceutical composition of the invention will vary, depending upon the identity, size, and/or condition of the subject treated and further depending upon the route by which the composition is to be administered.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters {e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable liposomes emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as polyethoxylated castor oil (e.g. CREMOPHOR™), alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. Alternatively, the preparation can be in the form of liposomes.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The peptides of the invention can be in micro-encapsulated form with one or more excipients as noted above. In one embodiment, the peptides of the invention are formulated in liposomes. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

It will be appreciated that peptides and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive conjugate useful for detecting tumors may be administered concurrently with another agent useful for detecting tumors), or they may achieve different effects (e.g., control of any adverse effects).

The pharmaceutical composition of the present invention may be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the peptide or pharmaceutical compositions in combination with agents that may improve their bioavailability, reduce and/or modify their metabolism, inhibit their excretion, and/or modify their distribution within the body.

The particular combination of therapies to employ in a combination regimen will take into account compatibility of the desired therapeutics and/or procedures and/or the desired therapeutic effect to be achieved. It will be appreciated that the therapies employed may achieve a desired effect for the same disorder (for example, an inventive polypeptide may be administered concurrently with another biologically active agent used to treat the same disorder), and/or they may achieve different effects (e.g., control of any adverse effects). In will further be appreciated that biologically active agents utilized in this combination may be administered together in a single composition or administered separately in different compositions.

The expression "in combination with" also encompasses the possibility of conjugating (by chemical-physical interactions) the peptide of the invention to any of the further agents mentioned above and below, which can be either a therapeutic agent or an agent for improving the profile of the peptide (such as bioavailability), among others.

In one embodiment, the peptides of the invention are administered in combination with one or more anti-cancer agents. An anti-cancer agent may be, for instance, methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, IS1641, ODN 698, TA 2516/Marmistat, BB2516/Marmistat, CDP 845, D2163, PD183805, DX895 if, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'-deoxycoformycin), Semustine (methyl-CCNU), Teniposide (VM-26) or Vindesine sulfate, signal transduction inhibitors (such as MEK, BRAF, AKT, her2, mTOR, and PI3K inhibitors), but it is not so limited.

As it is illustrated below, the peptides of the invention are useful in the treatment of cancer. In one embodiment, the peptides of formula (I) are useful in the treatment of glioblastomas. In another embodiment, the peptides of formula (XI) are useful in the treatment of lung cancer or glioblastomas.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

1. Materials and Methods
Synthetic General Procedure
Compounds IDP-wtLN10, IDP-intwtLN10 and IDP-NLCa02

Materials were purchased as following: Fmoc-protected α-amino acids (---); Rinkamide MBHA Resin (Tianjin Nankai HECHENG S&T Co., Ltd); HBTU ((2-(1H-benzotriazol-1-yl)-1,1,3,3-tetramethyluronium hexafluorophosphate), GL Biochem); N-methyl morpholine (Sinopharm Chemical Reagent Co., Ltd.); Succinic anhydride (Aladdin); acetonitrile (Xingke Chemical); ninhydrin (Sinopharm Chemical Reagent Co., Ltd.); Piperidine (Vertellus); Dimethylformamide, DMF (Zhejiang jiangshan chemical co., Ltd); trifluoroacetic acid, TFA (Trifluoroacetic acid, Solvay), TIS (Thioanisole, Solvay)

Briefly, the linear polypeptides were synthesized manually using Fmoc based SPPS (solid phase peptides synthesis) on Rink amide MBHA resin as support.

The following protocol was used:
1. The Fmoc protective group was removed with 20% piperidine in DMF.
2. The resin was washed with DMF five times.
3. The subsequent Fmoc-protected amino acid was coupled for 45 min using Fmoc-AA (3 equiv.), HBTU (3 equiv.), and N-methyl morpholine (6 equiv.).
4. The resin was washed with DMF five times. Coupling was checked by ninhydrin test.
5. Repeat from step 1.
6. N-terminal was capped by reacting with succinic anhydride (10 equiv.) and N-methyl morpholine (10 equiv.).

The peptide was cleaved from the resin and deprotected by exposure to solution F (95% TFA, 2,5% water, 2.5% TIS) and lyophilized.

The lyophilized peptides were purified by reverse phase HPLC using a C18 column (see compounds characterization for details). The peptides were identified by LC-MS-ESI. All the mass spectral data for all the compounds are shown below in Table 1.

Compounds IDP-SN02, IDP-SN10, IDP-SN16 and IDP-Na05

Materials were purchased as following: Fmoc-protected α-amino acids (include than the olefinic amino acids Fmoc-[(S)-2-(4 pentenyl)alanine]OH, Fmoc-[(R)-2-(4 pentenyl)alanine]OH, Fmoc-[(S)-2-(7 octenyl)alanine]OH, Fmoc-[(R)-2-(4 pentenyl)alanine]OH, 2-(6-chloro-1-H-benzotriazole-1-yl)-1,1,3,3-tetramethylaminium hexafluorophosphate (TBTU), resins, dimethylformamide (DMF), N,N-diisopropylethylamine (DIEA), trifluoroacetic acid (TFA), 1,2-dichloroethane (DCE), Grubbs Ru(IV) catalyst and piperidine were purchased from different suppliers.

Briefly, the linear polypeptides were synthesized with automatic synthesizer using Fmoc solid phase peptide chemistry. Only the coupling with olefinic amino acids was performed manually after removing the resins from the reactor vessel, as disclosed in the previous section.

The ring-closing metathesis reaction was performed in solution with a first generation Grubbs catalyst after cleaving the linear peptide from the resin, as disclosed by Scott J. M. and colleagues (Scott J. M. et al., "Application of Ring-Closing Metathesis to the Synthesis of Rigidified Amino Acids and Peptides", 1996, J. Am. Chem. Soc., 1996, 118 (40), pp 9606-9614).

The deprotected peptide precipitated with methyl-tert-butyl ether at 4° C. and lyophilized.

The lyophilized peptides were purified by reverse phase HPLC using a C18 column (see compounds characterization for details). The peptides were identified by LC-MS-ESI. All the mass spectral data for all the compounds are shown below in Table 1.

HPLC Conditions:

IDP-wtLN10. The compound was purified by HPLC-RP (C-18 column; Pump A: H$_2$O with 0.1% TFA; Pump B Acetonitrile with 0.1% TFA) using a linear gradient 20%-30% of B in 20 minutes (R. T.=11.79). Purity grade 98.70% by HPLC;

IDP-intwtLN10. The compound was purified by HPLC-RP (C-18 column; Pump A: H$_2$O with 0.1% TFA; Pump B Acetonitrile with 0.1% TFA) using a linear gradient 21%-31% of B in 20 minutes (R. T.=9.78). Purity grade 95.5% by HPLC;

IDP-NLCa02. The compound was purified by HPLC-RP (Sepax GP-C-18 column; Pump A: H$_2$O with 0.1% TFA; Pump B 80% Acetonitrile with 0.1% TFA) using a linear gradient 32%-42% of B in 20 minutes (R. T.=7.83). Purity grade 97.1% by HPLC;

IDP-NS02. The compound was purified by HPLC-RP (C-18 column; Pump A: H$_2$O with 0.1% TFA; Pump B Acetonitrile with 0.1% TFA) using a linear gradient 5%-60% of B in 22 minutes (R. T.=12.73). Purity grade 95.15% by HPLC;

IDP-NS10. The compound was purified by HPLC-RP (C-18 column; Pump A: H$_2$O with 0.1% TFA; Pump B Acetonitrile with 0.1% TFA) using a linear gradient 44%-54% of B in 15 minutes (R. T.=8.47). Purity grade 95,03% by HPLC;

IDP-NS16. The compound was purified by HPLC-RP (C-18 column; Pump A: H$_2$O with 0.1% TFA; Pump B Acetonitrile with 0.1% TFA) using a linear gradient 46%-56% of B in 20 minutes (R. T.=9.72). Purity grade 96.97% by HPLC;

IDP-Na05. The compound was purified by HPLC-RP (C-18 column; Pump A: H$_2$O with 0.1% TFA; Pump B Acetonitrile with 0.1% TFA) using a linear gradient 43%-63% of B in 20 minutes (R. T.=10.99). Purity grade 95.89% by HPLC.

TABLE 1 mass characterization

| N. ID | Sequence | | MW (1H) | Mass (2H) | Mass (3H) |
|---|---|---|---|---|---|
| IDP-wtLN10 | AAKVVILKKATEYVES | calcul. found | 1756.1 | 879.1 879.0 | 586.4 586.4 |
| IDP-intwtLN10 | RRRRRRRAAKVVILKKATEYVHS | calcul. found | 2849.5 | | 950.8 951.1 |
| IDP-NS02 | RQRRNKLRSKFLTLRDH | calcul. found | 2217.6 | | 740.2 740.2 |
| IDP-NS10 | AAXVVILKKXTEYVHS | calcul. found | 1849.26 | 925.6 924.7 | 617.4 617.0 |
| IDP-NS16 | RQRRNDLXSSFLTLXDH | calcul. found | 2149.44 | 1075.7 1075.0 | 717.5 717.1 |

| N. ID | Sequence | | Mass (4H) | Mass (5H) |
|---|---|---|---|---|
| IDP-wtLN10 | AAKVVILKKATEYVES | calcul. found | 440.0 440.1 | |
| IDP-intwtLN10 | RRRRRRRAAKVVILKKATEYVHS | calcul. found | 713.4 713.4 | 570.9 570.9 |
| IDP-NS02 | RQRRNKLRSKFLTLRDH | calcul. found | 555.4 555.5 | 444.5 444.7 |

TABLE 1-continued

| | mass characterization | | | |
|---|---|---|---|---|
| IDP-NS10 | AAXVVILK KXTEYVHS | calcul. found | | |
| IDP-NS16 | RQRRNDLX SSFLTLXD H | calcul. found | 538.4 538.2 | |

TABLE 1bis

| | | mass characterization | | | |
|---|---|---|---|---|---|
| N. ID | Sequence | | MW (1H) | Mass (2H) | Mass (3H) |
| IDP-NLCa02 | CPP2-RQ RRNDLRS SFLTLRD HVP | calcul. found | 4595.5 | | 1532.8 1532.2 |
| IDP-Na05 | RRNDLRS XFLTLRD XVP | calcul. found | 2149.6 | 1075.8 1075.7 | 717.5 717.5 |

| N. ID | Sequence | | Mass (4H) | Mass (5H) |
|---|---|---|---|---|
| IDP-NLCa02 | CPP2-RQRR NDLRSSFLT LRDHVP | calcul. found | 1149.9 1149.6 | 920.1 919.9 |
| IDP-Na05 | RRNDLRSXF LTLRDXVP | calcul. found | 538.4 538.4 | |

The X birradical represents the compound of formula:

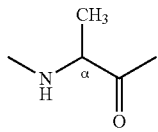

a L birradical corresponding to —$(CH_2)_3$—CH=CH—$(CH_2)_3$— (for the case of NS02) or —$(CH_2)_6$—CH=CH—$(CH_2)_3$— (for the cases NS10, NS16 and Na05) links both Xs radicals in each sequence, and CPP2 corresponds to penetratine peptide.

Cell Lines:
NCI-H524, lung (small cell lung cancer, SCLC), ATCC-CRL-5831
RG1, epithelial (glioblastoma, GMB), from surgical specimens from patients
GMB-27, epithelial (glioblastoma, GMB), from surgical specimens from patients
12O15, epithelial (glioblastoma, GMB), from surgical specimens from patients
12O53, epithelial (glioblastoma, GMB), from surgical specimens from patients
12O89, epithelial (glioblastoma, GMB), from surgical specimens from patients
RG6, epithelial (glioblastoma, GMB), from surgical specimens from patients
RG4, epithelial (glioblastoma, GMB), from surgical specimens from patients
RG5, epithelial (glioblastoma, GMB), from surgical specimens from patients Cell Culture
Cell lines NCI-H524 were cultured in incubator at 37° C. in RPMI-1640 (Sigma R8758) medium with 10% of fetal bovine serum inactivated (FBS) and 2 mM glutamine (Sigma G7513). Cell line RG1, RG4, RG5, RG6, 12O15, 12O89 and GBM-27 were cultured in incubator under $CO_2$ (6%) at 37° C. in complete medium (Neurobasal+B27+Glutamax+Growth factors).

During the amplification step and the assays adherent cells were rinsed with DPBS (Dulbecco's Phosphate Buffered Saline, Sigma D1283) three times and afterward treated for 5 minutes with trypsin ([0.5 g/ml]/EDTA [0.2 g/ml]) (Gibco-BRL, 15400054) in solution of DPBS at 37° C., and, once detached, transferred in the culturing medium. No-adherent cells were dissociated with Accumax, centrifuged and transferred in the culturing medium. Cells were counted in a Neubauer chamber after labelling with Tripan-Blue. Each assay was performed only when the viability was superior to 90%.

Viability Assay
NCI-H524 were seeded at a density of 2500 cells/well in 96 well plates; RG1, RG4, RG5, RG6, 12O15, 12O89 and GBM-27 were dissociated with Accumax and plate on p96 wells covered with Matrigel. After 24 h, the compounds to be tested were added to calculate the dose/response curve at the starting concentration of 100 μM with serial dilutions (1:1). Controls are the untreated cells. Each experiment was performed in triplicate.

Cells were incubated during 72-96 h in incubator under $CO_2$ atmosphere at 37° C. Cell viability was measured by means of Alamar Blue® (Biosource DAL1100) and CYTELL™, after treatment with Propidium iodide and Hoechst (GE Healthcare), following manufacturer instructions.

Assay proceeding follows:
Alamar Blue: 10 μl Alamar Blue solution was added to each well and the plates were incubated for 4 in the incubator. Fluorescence ratio at 535/590 (excitation/emission) was measured in Cytofluor (Millipore) fluorimeter. Blank control was determined by lysis of untreated cells with con 2% of Triton X100, right before adding Alamar Blue solution.

CYTELL™: 10 μl of propidium iodide and/or Hoechst solution was added to each well and the plates were incubated for 10 minutes protected by light. Control samples were represented by untreated cells and cell treated with 100% DMSO. Fluorescent stained cells which corresponds to death cells were detected by Cytell Imaging System and their amount calculated.

% Viability=Number of non-blue cells×100/Number of total cells

Statistics
Data analysis was performed calculating the percentage of cell viability normalized vs. the values of negative control, which was considered equal to 100%. The dose/response curve was fitted through the sigmoidal equation dose-response (variable slope) and the $EC_{50}$ values were calculated as follow:

$$Y=\text{Bottom}+(\text{Top}-\text{Bottom})/(1+10^{[(\log EC_{50}-X)*\text{HillSlope}]}),$$

where: X is compound concentration (log scale) and Y is the response

Calculations and graphs were conducted using GraphPad Prism (Prism 6 for Windows).

Mechanism of Action: Annexin V Assay by Flow Cytometry

Miltenyi Biotec Annexin V-FITC Kit was used. To detect apoptosis in early stage Phosphatidylserine in plasmatic membrane localization was measured, though the calcium dependent reaction with Annexine V. Annexin V molecules were labelled with different fluorophores (FITC) and analyzed by FACS. To detect apoptosis in late stage DNA-intercalating agents, such Propidium iodide (PI) were used.

Cells were seeded at a density range of 150000-30000 cells/well in 12 wells plates, and incubated at 37° C. in the incubator under $CO_2$ atmosphere. After 24 h, treatments at 96 hr were performed in cell lines RG1 at the concentration of 10 μM, with compounds IDP-SN10.

In Vivo Studies

Animals:

Nude immunosuppressed mice of 6-7 weeks old housed and handled in a pathogen-free zone (Instituto de Salud Carlos III, Hospital 12 de Octubre, Madrid). All experiments were carried out within the facilities of Hospital 12 de Octubre, Madrid.

Groups Studied:

Control: Medium (PBS) iv. 3 times per week.
IDP-NS1010 mg/kg i.v 3 times per week.

Methods and Follow-Up of the Study:

Subcutaneous xenograft model: The mice were inoculated subcutaneously with RG1 cells in in complete medium (Neurobasal+B27+Glutamax+Growth factors) and Matrigel® Basement Membrane Matrix. When the tumors became palpable, the mice were randomized into the different groups (6 mice in the control group and 6 in treated group) according to the tumor volume. This was estimated by measurements with a caliper of the two tumor diameters and using the following formula of a spheroid:

$$V=(a \cdot b^2 \cdot \pi)/6$$

where a and b correspond to the longest and shortest diameter, respectively. Tumor volume was monitored three times per week.

Survival evaluation: Mice were sacrificed when their tumor diameter reached a volume of 1100 m3. The time to reach the endpoint criterion was estimated from the day of treatment start; The statistical differences were evaluated using Kaplan-Meier curves with the log rank test. Statistical analyzes were performed using the SPSS-17.0 program.

2. Results 2.1 Efficacy Results

The experimental data are summarized in Tables 2 and 3 below:

TABLE 2 data for peptides of formula (I)

| Cell line | Active compound (EC50) | | |
|---|---|---|---|
| | IDP-wtLN10 | IDP-intwtLN10 | IDP-NS10 |
| RG1 | >100 | >100 | ≈7 |
| GBM27 | nt | nt | ≈7.5 |
| 12O15 | nt | nt | ≈10 |
| 12O89 | nt | nt | ≈4 |
| RG6 | nt | nt | ≈5 |
| RG4 | nt | nt | ≈5 |
| RG5 | nt | nt | ≈7 |
| 12O53 | >100 | >100 | ≈50 | n.t. = not-tested; EC50 expressed in μM

IDP-NS10 shows high anti-cancer activity in several glioblastoma cell lines, when compared with the wild type IDP-wtLN10.

TABLE 3 data for peptides of formula (II)

| Cell line | Active compound (EC50) | | | |
|---|---|---|---|---|
| | IDP-NS02 | IDP-NS16 | Na05 | NLCa02 |
| H524 | ≈5 | n.t. | n.t. | n.t. |
| RG1 | >100 | ≈15 | ≈10 | ≈5 |
| 12O53 | >100 | ≈10 | n.t. | n.t. | n.t. = not-tested; EC50 expressed in μM.

IDP-NS02, IDP-NS16, IDP-Na05 and IDP-NLCa02 also show anti-cancer activity in tumor cell lines.

2.2 Apoptosis Induction

RG1 cells were treated with the vehicle (control) and IDP-SN10 at 10 uM for 96 hr. The flow cytometry analysis for gated Annexin V and propidium iodine cells show an increment of the fraction of dead and apoptotic cell (expressed in %) after treatment with IDP-SN10, which indicates the induction of apoptosis due to the compound (Table 4).

TABLE 4

Flow cytometry data for peptides of formula (I)

| | Control | IDP-SN10 |
|---|---|---|
| Dead cells | 1.40% | 2.30% |
| Apoptotic cell | 2.20% | 9.80% |

2.3 Efficacy Results In Vivo

Tumor Growth

As can be seen in the Table 5, IDP-NS10 reduced significantly tumor growth with respect to the control. In particular, at the end-time (when the control in sacrificed) the tumor reduction corresponds to 53%.

TABLE 5

Comparison of the tumor volume between groups of untreated mice (control) and treated mice with IDP-NS10 i.v.

| | Group | Day of treatment | | | | |
|---|---|---|---|---|---|---|
| | | 1 | 7 | 9 | 14 | 19 |
| Normalized Tumor Volume (unit) | Control | 1 | 2 | 3 | 5.5 | 9 |
| | IDPN10 10 mg/kg | 1 | 1.3 | 1.7 | 2.3 | 4 |

As it is derived from these results, the administration of N10 peptide slows down cancer progression. Thus, it can be concluded that N10 can be used as anticancer drug alone or even in combination with chemo- or radiotherapy.

In view of the results provided above, the other peptides which have been in vitro tested, and which are active, are expected to work in the same way as N10.

For reasons of completeness, various aspects of the invention are set out in the following numbered clauses:

Clause 1. A peptide of formula (I) or a pharmaceutical salt thereof:

$$-[(Glu)m-(Lys)n-Ala-Ala-Lys-Val-Val-Ile-Leu-Lys-Lys-Ala-Thr-Glu-Tyr-Val-(His)p-(Ser)q]_r- \quad (I)$$

wherein
"m", "n", "p", and "q" represent integers and are selected from 0 and 1; and
"r" is comprised from 1 to 10;

the peptide comprising:

a linker birradical of formula (II)

which is connecting an alpha carbon atom of an amino acid located at position "i" in the peptide sequence of formula (I) with an alpha carbon atom of an amino acid located at position "i+4" or "i+7" in the peptide sequence of formula (I), a C-terminal end corresponding to —C(O)R$_4$; and
a N-terminal end corresponding to —NHR$_5$;

wherein

"a" and "b" are the same or different and are 0 or 1;
"c" is comprised from 1 to 10;
R$_1$ and R$_3$ are birradicals independently selected from the group consisting of: (C$_1$-C$_{10}$)alkyl; (C$_1$-C$_{10}$)alkyl substituted by one or more radicals selected from the group consisting of: halogen, (C$_1$-C$_{10}$)alkyl, —OR$_6$, —NR$_7$R$_8$, —SR$_9$, —SOR$_{10}$, —SO$_2$R$_{11}$, and —CO$_2$R$_{12}$; (C$_2$-C$_{10}$)alkenyl; (C$_2$-C$_{10}$)alkenyl substituted by one or more radicals selected from the group consisting of: halogen, (C$_1$-C$_{10}$)alkyl, —OR$_6$, —NR$_7$R$_8$, —SR$_9$, —SOR$_{10}$, —SO$_2$R$_{11}$, and —CO$_2$R$_{12}$; (C$_2$-C$_{10}$)alkynyl; and (C$_2$-C$_{10}$)alkinyl substituted by one or more radicals selected from the group consisting of: halogen, (C$_1$-C$_{10}$)alkyl, —OR$_6$, —NR$_1$R$_8$, —SR$_9$, —SOR$_{10}$, —SO$_2$R$_{11}$, and —CO$_2$R$_{12}$;

R$_2$ is a birradical selected from the group consisting of: —O—, C(═O), C(═O)NR$_{13}$, C(═O)O, S(═O), S(═O)$_2$, NR$_{14}$, (C$_1$-C$_{10}$)alkyl, (C$_2$-C$_{10}$)alkenyl, (C$_2$-C$_{10}$)alkynyl, —NR$_{15}$—NR$_{16}$—, —N═N—, —S—S—, and a known ring system comprising from 3 to 14 members, the system comprising from 1 to 3 rings, where:

each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—; and
the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—; and R$_4$ is a radical selected from the group consisting of —OH and —NR$_{17}$R$_{18}$;
R$_5$ is a radical selected from the group consisting of —H and (C$_1$-C$_{20}$)alkyl;

R$_6$, R$_7$, R$_8$, R$_9$, R$_{10}$, R$_{11}$, R$_{12}$, R$_{13}$, R$_{14}$, R$_{15}$, R$_{16}$, R$_{17}$ and R$_{18}$ are radicals independently selected from the group consisting of: —H and (C$_1$-C$_{10}$)alkyl; and the amino acids which are connected by the linker being of formula (III)

wherein

R$_{19}$ is a monoradical selected from the group consisting of: (C$_1$-C$_{10}$)alkyl, (C$_2$-C$_{10}$)alkenyl, (C$_2$-C$_{10}$)alkynyl, and a known ring system comprising from 3 to 14 members, the system comprising from 1 to 3 rings, where:

each one of the rings is saturated, partially unsaturated, or aromatic;
the rings are isolated, partially or totally fused,
each one of the members forming the known ring system is selected from the group consisting of: —CH—, —CH$_2$—, —NH—, —N—, —SH—, —S—, and —O—.

Clause 2. The peptide of formula (I) or a pharmaceutical salt thereof according to clause 1, wherein "r", "a", "b", and "c" are 1.

Clause 3. The peptide of formula (I) or a pharmaceutical salt thereof according to any one of the previous clauses, wherein R$_1$ and R$_3$ are birradicals independently selected from the group consisting of: (C$_1$-C$_{10}$)alkyl; (C$_2$-C$_{10}$)alkenyl; and (C$_2$-C$_{10}$)alkynyl.

Clause 4. The peptide of formula (I) or a pharmaceutical salt thereof according to any one of the previous clauses, wherein R$_2$ is a birradical selected from the group consisting of: (C$_1$-C$_{10}$)alkyl, (C$_2$-C$_{10}$)alkenyl, and (C$_2$-C$_{10}$)alkynyl.

Clause 5. The peptide of formula (I) or a pharmaceutical salt thereof according to any one of the previous clauses, wherein R$_{19}$ is a monoradical selected from the group consisting of: (C$_1$-C$_{10}$)alkyl, (C$_2$-C$_{10}$)alkenyl, and (C$_2$-C$_{10}$)alkynyl.

Clause 6. The peptide of formula (I) or a pharmaceutical salt thereof according to any one of the previous clauses, wherein R$_1$, R$_3$ and R$_{19}$ are (C$_1$-C$_{10}$)alkyl; R$_2$ is (C$_2$-C$_{10}$)alkenyl; "m" and "n" are the same; and "p" and "q" are the same.

Clause 7. The peptide of formula (I) or a pharmaceutical salt thereof according to any one of the previous clauses, wherein the C-terminal end corresponds to —C(O)OH or —C(O)NH$_2$, and the N-terminal end corresponds to —NH$_2$.

Clause 8. The peptide of formula (I) or a pharmaceutical salt thereof according to any one of the previous clauses, wherein the linker birradical of formula (II) is between an alpha carbon atom of an amino acid located at position "i" in the peptide sequence of formula (I) and an alpha carbon atom of an amino acid located at position "i+7" in the peptide sequence of formula (I), the peptide being of formula (Ia):

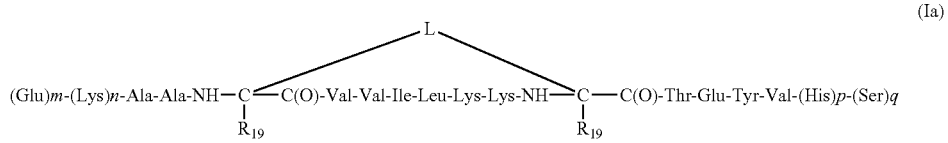

wherein "m", "n", "p", "q", L, and $R_{19}$ are as defined above.

Clause 9. The peptide of formula (I) or a pharmaceutical salt thereof according to any one of the previous clauses, which is of sequence SEQ ID NO: 3.

Clause 10. The peptide of formula (I) or a pharmaceutical salt thereof according to any one of the previous clauses, which is conjugated to a label or a drug.

Clause 11. A fusion protein comprising the peptide as defined in any one of the previous clauses and, optionally, a cell penetrating peptide.

Clause 12. A pharmaceutical composition comprising a therapeutically effective amount of the peptide or a pharmaceutical salt thereof as defined in any one of the clauses 1-10, or the fusion protein as defined in clause 11, together with acceptable pharmaceutical excipients and/or carriers.

Clause 13. A peptide or a pharmaceutical salt thereof as defined in any one of the clauses 1-10 or a fusion protein as defined in clause 11 for use as a medicament.

Clause 14. A peptide or a pharmaceutical salt thereof as defined in any one of the clauses 1-10 or a fusion protein as defined in clause 11 or the pharmaceutical composition as defined in clause 12 for use in the treatment of cancer.

Clause 15. The peptide or a pharmaceutical salt thereof for use according to clause 14, wherein the cancer is a glioblastoma.

CITATION LIST

Altschul et al., "Basic local alignment search tool", 1990, J. Mol. Biol, v. 215, pages 403-410;

Copolovici D. M. et al., "Cell-Penetrating Peptides: Design, Synthesis, and Applications", 2014, ACS Nano, 2014, 8 (3), pp 1972-1994;

Higgins et al., "CLUSTAL V: improved software for multiple sequence alignment", 1992, CABIOS, 8(2), pages 189-191;

Kim Young-Woo et al., "Synthesis of all-hydrocarbon stapled a-helical peptides by ring-closing olefin metathesis", Nature Protocols, 2011, 6(6), p. 761-771;

Kolb H. C. et al., "The growing impact of click chemistry on drug discovery", 2003, Drug Discov Today, 8(24):1128-1137); and Scott J. M. et al., "Application of Ring-Closing Metathesis to the Synthesis of Rigidified Amino Acids and Peptides", 1996, J. Am. Chem. Soc., 1996, 118 (40), pp 9606-9614;

---

The invention claimed is:

1. A peptide of formula (I) or a pharmaceutical salt thereof:

$$-[(Glu)_m-(Lys)_n-Ala-Ala-Lys-Val-Val-Ile-Leu-Lys-Lys-Ala-Thr-Glu-Tyr-Val-(His)_p-(Ser)_q]_r-\quad (I)$$

wherein

"m", "n", "p", and "q" represent integers and are selected from 0 and 1; and

"r" consists of integers from 1 to 3;

the peptide comprising:

a linker biradical "L" of formula (II)

$$-[(R_1)_a-(R_2)-(R_3)_b]_c-\quad (II)$$

which is connecting an alpha carbon atom of an amino acid located at position "i" in the peptide sequence of formula (I) with an alpha carbon atom of an amino acid located at position "i+4" or "i+7" in the peptide sequence of formula (I), a C-terminal end corresponding to —C(O)R$_4$; and a N-terminal end corresponding to —NHR$_5$;

wherein

"a" and "b" are the same or different and are 0 or 1;

"c" consists of integers from 1 to 10;

$R_1$ and $R_3$ are biradicals independently selected from the group consisting of: $(C_1-C_{10})$alkyl; $(C_1-C_{10})$alkyl substituted by one or more radicals selected from the group consisting of: halogen, $(C_1-C_{10})$alkyl, —OR$_6$, —NR$_7$R$_8$, —SR$_9$, —SOR$_{10}$, —SO$_2$R$_{11}$, and —CO$_2$R$_{12}$; $(C_2-C_{10})$alkenyl; $(C_2-C_{10})$alkenyl substituted by one or more radicals selected from the group consisting of: halogen, $(C_1-C_{10})$alkyl, —OR$_6$, —NR$_7$R$_8$, —SR$_9$, —SOR$_{10}$, —SO$_2$R$_{11}$, and —CO$_2$R$_{12}$; $(C_2-C_{10})$alkynyl; and $(C_2-C_{10})$alkynyl substituted by one or more radicals selected from the group consisting of: halogen, $(C_1-C_{10})$alkyl, —OR$_6$, —NR$_7$R$_8$, —SR$_9$, —SOR$_{10}$, —SO$_2$R$_{11}$, and —CO$_2$R$_{12}$;

$R_2$ is a biradical selected from the group consisting of: —O—, C(=O), C(=O)NR$_{13}$, C(=O)O, S(=O), S(=O)$_2$, NR$_{14}$, $(C_1-C_{10})$alkyl, $(C_2-C_{10})$alkenyl, $(C_2-C_{10})$alkynyl, —NR$_{15}$—NR$_{16}$—, —N=N—, —S—S—, and a known ring system consisting of from 3 to 14 members, the system consisting of from 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—; and the ring system is optionally substituted by one or more radicals independently selected from the group consisting of halogen, —OH, —NO$_2$, (C$_1$-C$_{10}$)alkyl, (C$_1$-C$_{10}$)haloalkyl, and (C$_1$-C$_{10}$)alkyl-O—; and R$_4$ is a radical selected from the group consisting of —OH and —NR$_{17}$R$_{18}$;

R$_5$ is a radical selected from the group consisting of —H and (C$_1$-C$_{20}$)alkyl;

R$_6$, R$_7$, R$_8$, R$_9$, R$_{10}$, R$_{11}$, R$_{12}$, R$_{13}$, R$_{14}$, R$_{15}$, R$_{16}$, R$_{17}$ and R$_{18}$ are radicals independently selected from the group consisting of: —H and (C$_1$-C$_{10}$)alkyl; and the amino acids which are connected by the linker being of formula (III)

wherein

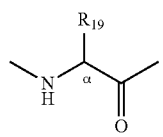

(III)

R$_{19}$ is a monoradical selected from the group consisting of: (C$_1$-C$_{10}$)alkyl, (C$_2$-C$_{10}$)alkenyl, (C$_2$-C$_{10}$)alkynyl, and a known ring system consisting of 3 to 14 members, the system consisting of 1 to 3 rings, where:

each one of the rings is saturated, partially unsaturated, or aromatic;

the rings are isolated, partially or totally fused, each one of the members forming the known ring system is selected from the group consisting of: —CH—, —CH$_2$—, —NH—, —N—, —SH—, —S—, and —O—;

or, alternatively, a peptide or a pharmaceutical salt thereof which consists of an amino acid sequence with an identity from 85% to 95% with respect to sequence SEQ ID NO: 9:

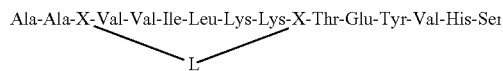

Ala-Ala-X-Val-Val-Ile-Leu-Lys-Lys-X-Thr-Glu-Tyr-Val-His-Ser wherein X is an amino acid of formula (III) as defined above and L is also as defined above, and wherein the peptide is characterized by having the linker L in the positions shown in SEQ ID NO: 9.

2. The peptide or pharmaceutical salt thereof according to claim 1, wherein "a", "b", and "c" are 1.

3. The peptide or pharmaceutical salt thereof according to claim 1, wherein R$_1$ and R$_3$ are biradicals independently selected from the group consisting of: (C$_1$-C$_{10}$)alkyl; (C$_2$-C$_{10}$)alkenyl; and (C$_2$-C$_{10}$)alkynyl.

4. The peptide or pharmaceutical salt thereof according to claim 1, wherein R$_2$ is a biradical selected from the group consisting of: (C$_1$-C$_{10}$)alkyl, (C$_2$-C$_{10}$)alkenyl, and (C$_2$-C$_{10}$)alkynyl.

5. The peptide or pharmaceutical salt thereof according to claim 1, wherein R$_{19}$ is a monoradical selected from the group consisting of: (C$_1$-C$_{10}$)alkyl, (C$_2$-C$_{10}$)alkenyl, and (C$_2$-C$_{10}$)alkynyl.

6. The peptide or pharmaceutical salt thereof according to claim 1, wherein R$_1$, R$_3$ and R$_{19}$ are (C$_1$-C$_{10}$)alkyl; R$_2$ is (C$_2$-C$_{10}$)alkenyl; "m" and "n" are the same; and "p" and "q" are the same.

7. The peptide or pharmaceutical salt thereof according to claim 1, wherein the C-terminal end corresponds to —C(O)OH or —C(O)NH$_2$, and the N-terminal end corresponds to —NH$_2$.

8. The peptide or pharmaceutical salt thereof according to claim 1 which is of formula (I) and "r" is 1.

9. The peptide or pharmaceutical salt thereof according to claim 1, which is of formula (I) and the linker biradical "L" of formula (II) is between an alpha carbon atom of an amino acid located at position "i" in the peptide sequence of formula (I) and an alpha carbon atom of an amino acid located at position "i+7" in the peptide sequence of formula (I), the peptide being of formula (Ia):

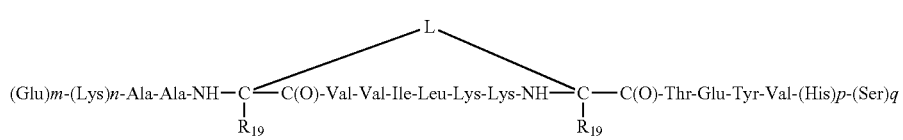

(Ia)

(Glu)$m$-(Lys)$n$-Ala-Ala-NH—C—C(O)-Val-Val-Ile-Leu-Lys-Lys-NH—C—C(O)-Thr-Glu-Tyr-Val-(His)$p$-(Ser)$q$
                              |                                               |
                              R$_{19}$                                          R$_{19}$ wherein "m", "n", "p", "q", L, and R$_{19}$ are as defined in claim 1.

10. The peptide or pharmaceutical salt thereof according to claim 1, which is of sequence SEQ ID NO: 3 or, alternatively, it is a peptide which has an amino acid sequence with an identity from 85% to 95% with respect sequence SEQ ID NO: 3.

11. The peptide or pharmaceutical salt thereof according to claim 1, which is conjugated to a label or a drug.

12. A fusion protein comprising the peptide as defined in claim 1 and a cell penetrating peptide.

13. A pharmaceutical composition comprising a therapeutically effective amount of the peptide or a pharmaceutical salt thereof as defined in claim 1, together with acceptable pharmaceutical excipients and/or carriers.

14. A method for treatment of cancer, comprising administering a therapeutically effective amount of the peptide or a pharmaceutical salt thereof as defined in claim 1, to a subject in need thereof.

15. The method according to claim 14, wherein the cancer is a glioblastoma or lung cancer.

* * * * *

SEQUENCE LISTING

```
<160> NUMBER OF SEQ ID NOS: 13

<210> SEQ ID NO 1
<211> LENGTH: 16
<212> TYPE: PRT
<213> ORGANISM: Artificial Sequence
<220> FEATURE:
<223> OTHER INFORMATION: peptide

<400> SEQUENCE: 1

Ala Ala Lys Val Val Ile Leu Lys Lys Ala Thr Glu Tyr Val His Ser
1               5                   10                  15

<210> SEQ ID NO 2
<211> LENGTH: 23
<212> TYPE: PRT
<213> ORGANISM: Artificial Sequence
<220> FEATURE:
<223> OTHER INFORMATION: peptide

<400> SEQUENCE: 2

Arg Arg Arg Arg Arg Arg Arg Ala Ala Lys Val Val Ile Leu Lys Lys
1               5                   10                  15

Ala Thr Glu Tyr Val His Ser
            20

<210> SEQ ID NO 3
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: the amino acid is of formula (III), being R19 a
      -CH3 radical; the alpha carbon of this amino acid being connected
      to the alpha carbon of amino acid at position 10, by the linker
      -(CH2)6-CH=CH-(CH2)3-
<220> FEATURE:
<221> NAME/KEY: MISC_FEATURE
<222> LOCATION: (10)..(10)
<223> OTHER INFORMATION: the amino acid is of formula (III), being R19 a
      -CH3 radical; the alpha carbon of this amino acid being connected
      to the alpha carbon of amino acid at position 3, by the linker
      -(CH2)6-CH=CH-(CH2)3-
```

```
<400> SEQUENCE: 3

Ala Ala Xaa Val Val Ile Leu Lys Lys Xaa Thr Glu Tyr Val His Ser
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (6)..(6)
<223> OTHER INFORMATION: the amino acid is of formula (III), being R19 a
      -CH3 radical; the alpha carbon of this amino acid being connected
      to the alpha carbon of amino acid at position 10, by the linker
      -(CH2)3-CH=CH-(CH2)3-
<220> FEATURE:
<221> NAME/KEY: MISC_FEATURE
<222> LOCATION: (10)..(10)
<223> OTHER INFORMATION: the amino acid is of formula (III), being R19 a
      -CH3 radical; the alpha carbon of this amino acid being connected
      to the alpha carbon of amino acid at position 6, by the linker
      -(CH2)3-CH=CH-(CH2)3-

<400> SEQUENCE: 4

Arg Gln Arg Arg Asn Xaa Leu Arg Ser Xaa Phe Leu Thr Leu Arg Asp
1               5                   10                  15

His

<210> SEQ ID NO 5
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (8)..(8)
<223> OTHER INFORMATION: the amino acid is of formula (III), being R19 a
      -CH3 radical; the alpha carbon of this amino acid being connected
      to the alpha carbon of amino acid at position 15, by the linker
      -(CH2)6-CH=CH-(CH2)3-
<220> FEATURE:
<221> NAME/KEY: MISC_FEATURE
<222> LOCATION: (15)..(15)
<223> OTHER INFORMATION: the amino acid is of formula (III), being R19 a
      -CH3 radical; the alpha carbon of this amino acid being connected
      to the alpha carbon of amino acid at position 8, by the linker
      -(CH2)6-CH=CH-(CH2)3-

<400> SEQUENCE: 5

Arg Gln Arg Arg Asn Asp Leu Xaa Ser Ser Phe Leu Thr Leu Xaa Asp
1               5                   10                  15

His

<210> SEQ ID NO 6
<211> LENGTH: 19
<212> TYPE: PRT
<213> ORGANISM: Artificial Sequence
<220> FEATURE:
<223> OTHER INFORMATION: peptide

<400> SEQUENCE: 6

Arg Gln Arg Arg Asn Asp Leu Arg Ser Ser Phe Leu Thr Leu Arg Asp
1               5                   10                  15

His Val Pro
```

```
<210> SEQ ID NO 7
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (8)..(8)
<223> OTHER INFORMATION: the amino acid is of formula (III), being R19 a
      -CH3 radical; the alpha carbon of this amino acid being connected
      to the alpha carbon of amino acid at position 15, by the linker
      -(CH2)6-CH=CH-(CH2)3-
<220> FEATURE:
<221> NAME/KEY: MISC_FEATURE
<222> LOCATION: (15)..(15)
<223> OTHER INFORMATION: the amino acid is of formula (III), being R19 a
      -CH3 radical; the alpha carbon of this amino acid being connected
      to the alpha carbon of amino acid at position 8, by the linker
      -(CH2)6-CH=CH-(CH2)3-

<400> SEQUENCE: 7

Arg Arg Asn Asp Leu Arg Ser Xaa Phe Leu Thr Leu Arg Asp Xaa Val
1               5                   10                  15

Pro

<210> SEQ ID NO 8
<211> LENGTH: 35
<212> TYPE: PRT
<213> ORGANISM: Artificial Sequence
<220> FEATURE:
<223> OTHER INFORMATION: peptide

<400> SEQUENCE: 8

Arg Gln Ile Lys Ile Trp Phe Gln Asn Arg Arg Met Lys Trp Lys Lys
1               5                   10                  15

Arg Gln Arg Arg Asn Asp Leu Arg Ser Ser Phe Leu Thr Leu Arg Asp
            20                  25                  30

His Val Pro
        35

<210> SEQ ID NO 9
<211> LENGTH: 16
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: the amino acid is of formula (III) as defined
      in claim 1; the alpha carbon of this amino acid being connected to
      the alpha carbon of amino acid at position 10, by the linker "L"
      as defined in claim 1
<220> FEATURE:
<221> NAME/KEY: MISC_FEATURE
<222> LOCATION: (10)..(10)
<223> OTHER INFORMATION: the amino acid is of formula (III) as defined
      in claim 1; the alpha carbon of this amino acid being connected to
      the alpha carbon of amino acid at position 3, by the linker "L" as
      defined in claim 1

<400> SEQUENCE: 9

Ala Ala Xaa Val Val Ile Leu Lys Lys Xaa Thr Glu Tyr Val His Ser
1               5                   10                  15

<210> SEQ ID NO 10
<211> LENGTH: 17
<212> TYPE: PRT
<213> ORGANISM: Artificial Sequence
```

```
<220> FEATURE:
<223> OTHER INFORMATION: peptide
<220> FEATURE:
<221> NAME/KEY: MISC_FEATURE
<222> LOCATION: (6)..(6)
<223> OTHER INFORMATION: the amino acid is of formula (III) as defined
      in claim 1; the alpha carbon of this amino acid being connected to
      the alpha carbon of amino acid at position 10, by the linker "L"
      as defined in claim 1
<220> FEATURE:
<221> NAME/KEY: MISC_FEATURE
<222> LOCATION: (10)..(10)
<223> OTHER INFORMATION: the amino acid is of formula (III) as defined
      in claim 1; the alpha carbon of this amino acid being connected to
      the alpha carbon of amino acid at position 6, by the linker "L" as
      defined in claim 1

<400> SEQUENCE: 10

Arg Gln Arg Arg Asn Xaa Leu Arg Ser Xaa Phe Leu Thr Leu Arg Asp
1               5                   10                  15

His

<210> SEQ ID NO 11
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (8)..(8)
<223> OTHER INFORMATION: the amino acid is of formula (III) as defined
      in claim 1; the alpha carbon of this amino acid being connected to
      the alpha carbon of amino acid at position 15, by the linker "L"
      as defined in claim 1
<220> FEATURE:
<221> NAME/KEY: MISC_FEATURE
<222> LOCATION: (15)..(15)
<223> OTHER INFORMATION: the amino acid is of formula (III) as defined
      in claim 1; the alpha carbon of this amino acid being connected to
      the alpha carbon of amino acid at position 8, by the linker "L" as
      defined in claim 1

<400> SEQUENCE: 11

Arg Gln Arg Arg Asn Asp Leu Xaa Ser Ser Phe Leu Thr Leu Xaa Asp
1               5                   10                  15

His

<210> SEQ ID NO 12
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (8)..(8)
<223> OTHER INFORMATION: the amino acid is of formula (III) as defined
      in claim 1; the alpha carbon of this amino acid being connected to
      the alpha carbon of amino acid at position 15, by the linker "L"
      as defined in claim 1
<220> FEATURE:
<221> NAME/KEY: MISC_FEATURE
<222> LOCATION: (15)..(15)
<223> OTHER INFORMATION: the amino acid is of formula (III) as defined
      in claim 1; the alpha carbon of this amino acid being connected to
      the alpha carbon of amino acid at position 8, by the linker "L" as
      defined in claim 1
```

```
<400> SEQUENCE: 12

Arg Arg Asn Asp Leu Arg Ser Xaa Phe Leu Thr Leu Arg Asp Xaa Val
1               5                   10                  15

Pro

<210> SEQ ID NO 13
<211> LENGTH: 19
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: 1
<223> OTHER INFORMATION: Amino acid at position 1 can be either present
      or absent
<220> FEATURE:
<221> NAME/KEY: misc_feature
<222> LOCATION: 2
<223> OTHER INFORMATION: Amino acid at position 2 can be either present
      or absent
<220> FEATURE:
<221> NAME/KEY: misc_feature
<222> LOCATION: 18
<223> OTHER INFORMATION: Amino acid at position 18 can be either present
      or absent
<220> FEATURE:
<221> NAME/KEY: misc_feature
<222> LOCATION: 19
<223> OTHER INFORMATION: Amino acid at position 19 can be either present
      or absent

<400> SEQUENCE: 13

Arg Gln Arg Arg Asn Asp Leu Arg Ser Ser Phe Leu Thr Leu Arg Asp
1               5                   10                  15

His Val Pro
```